(12) United States Patent
Evans

(10) Patent No.: US 8,845,512 B2
(45) Date of Patent: Sep. 30, 2014

(54) SLING ANCHOR SYSTEM

(75) Inventor: Douglas G. Evans, Snellville, GA (US)

(73) Assignee: C. R. Bard, Inc., Murray Hill, NJ (US)

(*) Notice: Subject to any disclaimer, the term of this patent is extended or adjusted under 35 U.S.C. 154(b) by 0 days.

(21) Appl. No.: 13/345,512

(22) Filed: Jan. 6, 2012

(65) Prior Publication Data

US 2012/0108890 A1 May 3, 2012

Related U.S. Application Data

(63) Continuation of application No. 12/093,493, filed as application No. PCT/US2006/044315 on Nov. 14, 2006, now Pat. No. 8,092,366.

(60) Provisional application No. 60/736,219, filed on Nov. 14, 2005, provisional application No. 60/749,774, filed on Dec. 13, 2005, provisional application No. 60/754,540, filed on Dec. 28, 2005.

(51) Int. Cl.
| | |
|---|---|
| *A61F 2/02* | (2006.01) |
| *A61B 17/04* | (2006.01) |
| *A61B 17/06* | (2006.01) |
| *A61F 2/00* | (2006.01) |
| *A61B 17/00* | (2006.01) |
| *A61F 2/30* | (2006.01) |

(52) U.S. Cl.
CPC ....... *A61F 2/0045* (2013.01); *A61F 2250/0087* (2013.01); *A61B 17/0401* (2013.01); *A61B 2017/0409* (2013.01); *A61B 17/06109* (2013.01); *A61B 2017/0608* (2013.01); *A61B 2017/00805* (2013.01); *A61B 2017/061* (2013.01); *A61F 2002/30713* (2013.01); *A61B 17/06066* (2013.01); *A61B 2017/00477* (2013.01)
USPC .......................................... 600/30

(58) Field of Classification Search
USPC .......... 600/29–32, 37; 128/885; 606/151, 157
See application file for complete search history.

(56) References Cited

U.S. PATENT DOCUMENTS

| | | | |
|---|---|---|---|
| 107,956 | A | 10/1870 | Peoble |
| 1,393,107 | A | 10/1921 | Fuller |
| 1,450,101 | A | 3/1923 | Mathewson |
| 1,758,261 | A | 5/1930 | Leland |
| 1,924,348 | A | 8/1933 | Brown |
| 2,042,403 | A | 5/1936 | Hrivnak |

(Continued)

FOREIGN PATENT DOCUMENTS

| | | |
|---|---|---|
| CA | 2592617 C | 1/2012 |
| CN | 101854883 A | 10/2010 |

(Continued)

OTHER PUBLICATIONS

Scotti, RJ, et al., "Paravaginal repair of lateral vaginal wall defects by fixation to the ischial periosteum and obturator membrane," Am J Obstet Gynecol. Dec. 1998;179(6 Pt 1):1436-45.

(Continued)

*Primary Examiner* — Christine Matthews
(74) *Attorney, Agent, or Firm* — Rutan & Tucker, LLP

(57) ABSTRACT

The present disclosure is generally directed to surgical articles useful for implanting support members in patients. The articles disclosed herein include a support member, such as a sling for urinary incontinence, tissue anchors, filamentary elements for associating the support member with the anchors, and introducer needles for placing the anchors in a patient. The support members can also be configured for use in pelvic floor repair, such as for treating cystoceles, rectoceles, and enteroceles.

12 Claims, 21 Drawing Sheets

(56) References Cited

U.S. PATENT DOCUMENTS

| | | |
|---|---|---|
| 2,097,018 A | 10/1937 | Chamberlin |
| 2,137,710 A | 11/1938 | Anderson |
| 2,240,330 A | 4/1941 | Flagg et al. |
| 2,427,176 A | 9/1947 | Aldeen |
| 2,518,994 A | 8/1950 | Miller |
| 2,641,249 A | 6/1953 | Brockman |
| 2,666,338 A | 1/1954 | Sandberg |
| 2,738,790 A | 3/1956 | Todt et al. |
| 3,124,136 A | 3/1964 | Usher |
| 3,126,600 A | 3/1964 | De Marre |
| 3,182,662 A | 5/1965 | Shirodkar |
| 3,249,104 A | 5/1966 | Johnstein |
| 3,311,110 A | 3/1967 | Singerman et al. |
| 3,340,494 A | 9/1967 | Gutshall |
| 3,384,073 A | 5/1968 | Van Winkle, Jr. |
| 3,453,729 A | 7/1969 | Larson |
| 3,472,232 A | 10/1969 | Earl |
| 3,580,313 A | 5/1971 | McKnight |
| 3,714,843 A | 2/1973 | Bracey |
| 3,739,430 A | 6/1973 | Kohke |
| 3,763,860 A | 10/1973 | Clarke |
| 3,777,737 A | 12/1973 | Bucalo |
| 3,789,828 A | 2/1974 | Schulte |
| 3,858,783 A | 1/1975 | Kapitanov et al. |
| 3,913,179 A | 10/1975 | Rhee |
| 3,924,633 A | 12/1975 | Cook et al. |
| 3,976,351 A | 8/1976 | Hopfe |
| 3,995,619 A | 12/1976 | Glatzer |
| 4,019,499 A | 4/1977 | Fitzgerald |
| 4,037,603 A | 7/1977 | Wendorff |
| 4,063,356 A | 12/1977 | Hepworth et al. |
| 4,069,956 A | 1/1978 | Shearer, Sr. et al. |
| 4,089,112 A | 5/1978 | Richards |
| 4,128,100 A | 12/1978 | Wendorff |
| 4,172,458 A | 10/1979 | Pereyra |
| 4,204,541 A | 5/1980 | Kapitanov |
| 4,232,445 A | 11/1980 | Ito et al. |
| 4,233,734 A | 11/1980 | Bies |
| 4,235,238 A | 11/1980 | Ogiu et al. |
| 4,246,660 A | 1/1981 | Wevers |
| 4,255,881 A | 3/1981 | Fralish |
| 4,258,716 A | 3/1981 | Sutherland et al. |
| 4,265,231 A | 5/1981 | Scheller, Jr. et al. |
| 4,281,660 A | 8/1981 | Fujiwara |
| 4,322,885 A | 4/1982 | Osada et al. |
| 4,361,958 A | 12/1982 | Gilbert et al. |
| 4,409,866 A | 10/1983 | McBride |
| 4,441,497 A | 4/1984 | Paudler |
| 4,452,245 A | 6/1984 | Usher |
| 4,455,690 A | 6/1984 | Homsy |
| 4,467,802 A | 8/1984 | Maslanka et al. |
| 4,509,516 A | 4/1985 | Richmond |
| 4,524,771 A | 6/1985 | McGregor et al. |
| 4,632,100 A | 12/1986 | Somers et al. |
| 4,655,221 A | 4/1987 | Devereux |
| 4,679,453 A | 7/1987 | Morita et al. |
| 4,712,458 A | 12/1987 | Mally |
| 4,718,419 A | 1/1988 | Okada et al. |
| 4,741,335 A | 5/1988 | Okada et al. |
| 4,773,416 A | 9/1988 | Hourahane |
| 4,775,380 A | 10/1988 | Seedhom et al. |
| 4,784,139 A | 11/1988 | Demos |
| 4,799,484 A | 1/1989 | Smith et al. |
| 4,857,041 A | 8/1989 | Annis et al. |
| 4,865,031 A | 9/1989 | O'Keeffe |
| 4,911,164 A | 3/1990 | Roth |
| 4,920,986 A | 5/1990 | Biswas |
| 4,938,760 A | 7/1990 | Burton et al. |
| 4,946,467 A | 8/1990 | Ohi et al. |
| 5,013,292 A | 5/1991 | Lemay et al. |
| 5,013,316 A | 5/1991 | Goble et al. |
| 5,026,371 A | 6/1991 | Rydell et al. |
| 5,027,674 A | 7/1991 | Nolte et al. |
| 5,029,489 A | 7/1991 | Burmeister et al. |
| 5,053,043 A | 10/1991 | Gottesman et al. |
| 5,084,054 A | 1/1992 | Bencini et al. |
| 5,085,661 A | 2/1992 | Moss |
| 5,112,344 A | 5/1992 | Petros |
| 5,122,155 A | 6/1992 | Eberbach |
| 5,123,428 A | 6/1992 | Schwarz |
| 5,123,910 A | 6/1992 | McIntosh |
| 5,149,329 A | 9/1992 | Richardson |
| 5,152,749 A | 10/1992 | Giesy et al. |
| 5,152,778 A | 10/1992 | Bales, Jr. et al. |
| 5,163,942 A | 11/1992 | Rydell |
| 5,171,233 A | 12/1992 | Amplatz et al. |
| 5,171,314 A | 12/1992 | Dulebohn |
| 5,188,636 A | 2/1993 | Fedotov |
| 5,201,741 A | 4/1993 | Dulebohn |
| 5,207,694 A | 5/1993 | Broome |
| 5,209,756 A | 5/1993 | Seedhom et al. |
| 5,234,436 A | 8/1993 | Eaton et al. |
| 5,246,452 A | 9/1993 | Sinnott |
| 5,250,033 A | 10/1993 | Evans et al. |
| 5,256,133 A | 10/1993 | Spitz |
| 5,269,063 A | 12/1993 | Okada et al. |
| 5,281,237 A | 1/1994 | Gimpelson |
| 5,304,187 A | 4/1994 | Green et al. |
| 5,311,858 A | 5/1994 | Adair |
| 5,328,077 A | 7/1994 | Lou |
| 5,333,624 A | 8/1994 | Tovey |
| 5,334,185 A | 8/1994 | Giesy et al. |
| 5,336,239 A | 8/1994 | Gimpelson |
| 5,337,736 A | 8/1994 | Reddy |
| 5,342,371 A | 8/1994 | Welter et al. |
| 5,356,432 A | 10/1994 | Rutkow et al. |
| 5,362,294 A | 11/1994 | Seitzinger |
| 5,368,595 A | 11/1994 | Lewis |
| 5,368,602 A | 11/1994 | de la Torre |
| 5,380,334 A | 1/1995 | Torrie et al. |
| 5,383,904 A | 1/1995 | Totakura et al. |
| 5,386,836 A | 2/1995 | Biswas |
| 5,397,332 A | 3/1995 | Kammerer et al. |
| 5,397,353 A | 3/1995 | Oliver et al. |
| 5,403,328 A | 4/1995 | Shallman |
| 5,413,598 A | 5/1995 | Moreland |
| 5,439,467 A | 8/1995 | Benderev et al. |
| 5,447,512 A | 9/1995 | Wilson et al. |
| 5,456,721 A | 10/1995 | Legrand |
| 5,473,796 A | 12/1995 | Fusillo |
| 5,474,543 A | 12/1995 | McKay |
| 5,486,183 A | 1/1996 | Middleman et al. |
| 5,497,553 A | 3/1996 | Chong et al. |
| 5,499,991 A | 3/1996 | Garman et al. |
| 5,500,000 A | 3/1996 | Feagin et al. |
| 5,501,692 A | 3/1996 | Riza |
| 5,502,896 A | 4/1996 | Chen et al. |
| 5,509,900 A | 4/1996 | Kirkman |
| 5,520,700 A | 5/1996 | Beyar et al. |
| 5,520,703 A | 5/1996 | Essig et al. |
| 5,522,833 A | 6/1996 | Stephens et al. |
| 5,542,948 A | 8/1996 | Weaver et al. |
| 5,544,664 A | 8/1996 | Benderev et al. |
| 5,549,619 A | 8/1996 | Peters et al. |
| 5,549,676 A | 8/1996 | Johnson |
| 5,562,678 A | 10/1996 | Booker |
| 5,562,685 A | 10/1996 | Mollenauer et al. |
| 5,562,688 A | 10/1996 | Riza |
| 5,562,689 A | 10/1996 | Green et al. |
| 5,569,269 A | 10/1996 | Hart et al. |
| 5,571,139 A | 11/1996 | Jenkins, Jr. |
| 5,573,530 A | 11/1996 | Fleury et al. |
| 5,591,163 A | 1/1997 | Thompson |
| 5,601,558 A | 2/1997 | Torrie et al. |
| 5,611,515 A | 3/1997 | Benderev et al. |
| 5,628,756 A | 5/1997 | Barker, Jr. et al. |
| 5,633,286 A | 5/1997 | Chen |
| 5,640,886 A | 6/1997 | Lai et al. |
| 5,643,320 A | 7/1997 | Lower et al. |
| 5,647,836 A | 7/1997 | Blake, III et al. |
| 5,655,270 A | 8/1997 | Boisvert |
| 5,662,683 A | 9/1997 | Kay |
| 5,667,513 A | 9/1997 | Torrie et al. |
| 5,669,935 A | 9/1997 | Rosenman et al. |

(56) References Cited

U.S. PATENT DOCUMENTS

| | | |
|---|---|---|
| 5,683,349 A | 11/1997 | Makower et al. |
| 5,689,860 A | 11/1997 | Matoba et al. |
| 5,693,072 A | 12/1997 | McIntosh |
| 5,702,397 A | 12/1997 | Goble et al. |
| 5,755,728 A | 5/1998 | Maki |
| 5,774,994 A | 7/1998 | Stein et al. |
| 5,792,142 A | 8/1998 | Galitzer |
| 5,807,403 A | 9/1998 | Beyar et al. |
| 5,810,882 A | 9/1998 | Bolduc et al. |
| 5,817,104 A | 10/1998 | Bilitz et al. |
| 5,817,128 A | 10/1998 | Storz et al. |
| 5,830,220 A | 11/1998 | Wan et al. |
| 5,836,053 A | 11/1998 | Davignon et al. |
| 5,836,314 A | 11/1998 | Benderev et al. |
| 5,836,315 A | 11/1998 | Benderev et al. |
| 5,840,011 A | 11/1998 | Landgrebe et al. |
| 5,842,478 A | 12/1998 | Benderev et al. |
| 5,846,248 A | 12/1998 | Chu et al. |
| 5,860,425 A | 1/1999 | Benderev et al. |
| 5,862,596 A | 1/1999 | Chung et al. |
| 5,864,952 A | 2/1999 | Chung et al. |
| 5,899,909 A | 5/1999 | Claren et al. |
| 5,904,692 A | 5/1999 | Steckel et al. |
| 5,904,696 A | 5/1999 | Rosenman |
| 5,910,148 A | 6/1999 | Reimels et al. |
| 5,919,232 A | 7/1999 | Chaffringeon et al. |
| 5,934,283 A | 8/1999 | Willem et al. |
| 5,935,122 A | 8/1999 | Fourkas et al. |
| 5,935,138 A | 8/1999 | McJames, II et al. |
| 5,944,732 A | 8/1999 | Raulerson et al. |
| 5,947,978 A | 9/1999 | Holsinger |
| 5,961,526 A | 10/1999 | Chu et al. |
| 5,968,008 A | 10/1999 | Grams |
| 5,971,967 A | 10/1999 | Willard |
| 5,972,000 A | 10/1999 | Beyar et al. |
| 5,987,751 A | 11/1999 | Chung |
| 5,988,171 A | 11/1999 | Sohn et al. |
| 5,992,269 A | 11/1999 | Puig et al. |
| 5,993,459 A | 11/1999 | Larsen et al. |
| 5,997,554 A | 12/1999 | Thompson |
| 6,005,191 A | 12/1999 | Tzeng et al. |
| 6,006,433 A | 12/1999 | Baltazar |
| 6,010,447 A | 1/2000 | Kardjian |
| 6,030,393 A | 2/2000 | Corlew |
| 6,031,148 A | 2/2000 | Hayes et al. |
| 6,039,686 A | 3/2000 | Kovac |
| 6,042,534 A | 3/2000 | Gellman et al. |
| 6,042,536 A | 3/2000 | Tihon et al. |
| 6,048,351 A | 4/2000 | Gordon et al. |
| 6,048,354 A | 4/2000 | Lawrence |
| 6,050,937 A | 4/2000 | Benderev |
| 6,053,925 A | 4/2000 | Barnhart |
| 6,053,935 A | 4/2000 | Brenneman et al. |
| 6,056,688 A | 5/2000 | Benderev et al. |
| 6,059,796 A | 5/2000 | Bilitz et al. |
| 6,063,094 A | 5/2000 | Rosenberg et al. |
| 6,068,591 A | 5/2000 | Bruckner et al. |
| 6,068,648 A | 5/2000 | Cole et al. |
| 6,071,290 A | 6/2000 | Compton |
| 6,074,341 A | 6/2000 | Anderson et al. |
| 6,086,591 A | 7/2000 | Bojarski |
| 6,092,955 A | 7/2000 | Chartrain et al. |
| 6,096,041 A | 8/2000 | Gellman et al. |
| 6,096,060 A | 8/2000 | Fitts et al. |
| 6,099,538 A | 8/2000 | Moses et al. |
| 6,106,545 A | 8/2000 | Egan |
| 6,110,101 A | 8/2000 | Tihon et al. |
| 6,117,067 A | 9/2000 | Gil-Vernet |
| 6,117,162 A | 9/2000 | Schmieding et al. |
| 6,168,611 B1 | 1/2001 | Rizvi |
| 6,171,315 B1 | 1/2001 | Chu et al. |
| 6,197,036 B1 | 3/2001 | Tripp et al. |
| 6,200,330 B1 | 3/2001 | Benderev et al. |
| 6,210,416 B1 | 4/2001 | Chu et al. |
| 6,221,005 B1 | 4/2001 | Bruckner et al. |
| 6,221,060 B1 | 4/2001 | Willard |
| 6,226,873 B1 | 5/2001 | Okumura et al. |
| 6,235,026 B1 | 5/2001 | Smith |
| 6,273,852 B1 | 8/2001 | Lehe et al. |
| 6,290,702 B1 | 9/2001 | Fucci et al. |
| 6,293,961 B2 | 9/2001 | Schwartz et al. |
| 6,302,840 B1 | 10/2001 | Benderev |
| 6,306,079 B1 | 10/2001 | Trabucco |
| 6,306,159 B1 | 10/2001 | Schwartz et al. |
| 6,312,448 B1 | 11/2001 | Bonutti |
| 6,315,782 B1 | 11/2001 | Chu et al. |
| 6,319,271 B1 | 11/2001 | Schwartz et al. |
| 6,322,492 B1 | 11/2001 | Kovac |
| 6,328,686 B1 | 12/2001 | Kovac |
| 6,328,744 B1 | 12/2001 | Harari et al. |
| 6,328,758 B1 | 12/2001 | Tornier et al. |
| 6,334,446 B1 | 1/2002 | Beyar |
| 6,336,731 B1 | 1/2002 | Chien |
| 6,346,109 B1 | 2/2002 | Fucci et al. |
| 6,346,115 B1 | 2/2002 | Lawrence |
| 6,352,553 B1 | 3/2002 | van der Burg et al. |
| 6,355,065 B1 | 3/2002 | Gabbay |
| 6,358,197 B1 | 3/2002 | Silverman et al. |
| 6,367,353 B2 | 4/2002 | Brucart Puig et al. |
| 6,371,963 B1 | 4/2002 | Nishtala et al. |
| 6,375,661 B2 | 4/2002 | Chu et al. |
| 6,382,214 B1 | 5/2002 | Raz et al. |
| D458,679 S | 6/2002 | Thompson et al. |
| 6,406,423 B1 | 6/2002 | Scetbon et al. |
| 6,406,480 B1 | 6/2002 | Beyar et al. |
| 6,409,733 B1 | 6/2002 | Conlon et al. |
| 6,423,080 B1 | 7/2002 | Gellman et al. |
| 6,432,123 B2 | 8/2002 | Schwartz et al. |
| 6,440,154 B2 | 8/2002 | Gellman et al. |
| 6,475,139 B1 | 11/2002 | Miller |
| 6,478,727 B2 | 11/2002 | Scetbon et al. |
| 6,478,803 B1 | 11/2002 | Kapec et al. |
| 6,482,214 B1 | 11/2002 | Sidor, Jr. et al. |
| 6,491,703 B1 | 12/2002 | Ulmsten et al. |
| 6,491,714 B1 | 12/2002 | Bennett |
| 6,494,887 B1 | 12/2002 | Kaladelfos et al. |
| 6,494,906 B1 | 12/2002 | Owens |
| 6,502,578 B2 | 1/2003 | Raz et al. |
| 6,506,190 B1 | 1/2003 | Walshe |
| 6,511,499 B2 | 1/2003 | Schmieding et al. |
| 6,517,552 B1 | 2/2003 | Nord et al. |
| 6,530,943 B1 | 3/2003 | Hoepffner et al. |
| 6,537,198 B1 | 3/2003 | Vidlund et al. |
| 6,544,267 B1 | 4/2003 | Cole et al. |
| 6,553,674 B1 | 4/2003 | Budrow |
| 6,554,842 B2 | 4/2003 | Heuser et al. |
| 6,569,188 B2 | 5/2003 | Grafton et al. |
| 6,575,976 B2 | 6/2003 | Grafton |
| 6,575,984 B2 | 6/2003 | Beyar et al. |
| 6,575,998 B2 | 6/2003 | Beyar et al. |
| 6,582,443 B2 | 6/2003 | Cabak et al. |
| 6,591,838 B2 | 7/2003 | Durgin |
| 6,592,515 B2 | 7/2003 | Thierfelder et al. |
| 6,592,610 B2 | 7/2003 | Beyar et al. |
| 6,596,001 B2 | 7/2003 | Stormby et al. |
| 6,605,097 B1 | 8/2003 | Lehe et al. |
| 6,612,977 B2 | 9/2003 | Staskin et al. |
| 6,626,917 B1 | 9/2003 | Craig |
| 6,638,209 B2 | 10/2003 | Landgrebe et al. |
| 6,638,210 B2 | 10/2003 | Berger |
| 6,638,211 B2 | 10/2003 | Suslian et al. |
| 6,638,286 B1 | 10/2003 | Burbank et al. |
| 6,641,524 B2 | 11/2003 | Kovac |
| 6,641,525 B2 | 11/2003 | Rocheleau et al. |
| 6,652,450 B2 | 11/2003 | Neisz et al. |
| 6,652,537 B2 | 11/2003 | Mercereau et al. |
| 6,656,183 B2 | 12/2003 | Colleran et al. |
| 6,663,633 B1 | 12/2003 | Pierson, III |
| 6,663,645 B2 | 12/2003 | Nishtala et al. |
| 6,673,010 B2 | 1/2004 | Skiba et al. |
| 6,675,483 B2 | 1/2004 | Bond et al. |
| 6,676,668 B2 | 1/2004 | Mercereau et al. |
| 6,685,629 B2 | 2/2004 | Therin |
| 6,689,047 B2 | 2/2004 | Gellman |

(56) References Cited

U.S. PATENT DOCUMENTS

| | | |
|---|---|---|
| 6,691,711 B2 | 2/2004 | Raz et al. |
| 6,702,827 B1 | 3/2004 | Lund et al. |
| 6,708,410 B2 | 3/2004 | Okada et al. |
| 6,712,830 B2 | 3/2004 | Esplin |
| 6,730,097 B2 | 5/2004 | Dennis |
| 6,730,110 B1 | 5/2004 | Harari et al. |
| 6,736,854 B2 | 5/2004 | Vadurro et al. |
| 6,737,371 B1 | 5/2004 | Planck et al. |
| 6,746,472 B2 | 6/2004 | Frazier et al. |
| 6,752,814 B2 | 6/2004 | Gellman et al. |
| 6,755,781 B2 | 6/2004 | Gellman |
| 6,761,722 B2 | 7/2004 | Cole et al. |
| 6,789,326 B1 | 9/2004 | Huang et al. |
| 6,802,807 B2 | 10/2004 | Anderson et al. |
| 6,808,486 B1 | 10/2004 | O'Donnell |
| 6,808,487 B2 | 10/2004 | Migliari et al. |
| 6,835,193 B2 | 12/2004 | Epstein et al. |
| 6,843,792 B2 | 1/2005 | Nishtala et al. |
| 6,872,227 B2 | 3/2005 | Sump et al. |
| 6,878,134 B2 | 4/2005 | Rogers et al. |
| 6,881,184 B2 | 4/2005 | Zappala |
| 6,908,425 B2 | 6/2005 | Luscombe |
| 6,911,003 B2 | 6/2005 | Anderson et al. |
| 6,932,759 B2 | 8/2005 | Kammerer et al. |
| 6,936,052 B2 | 8/2005 | Gellman et al. |
| 6,953,428 B2 | 10/2005 | Gellman et al. |
| 6,960,160 B2 | 11/2005 | Browning et al. |
| 6,966,113 B2 | 11/2005 | Fossella |
| 6,971,390 B1 | 12/2005 | Vasek et al. |
| 6,971,986 B2 | 12/2005 | Staskin et al. |
| 6,986,781 B2 | 1/2006 | Smith |
| 6,987,995 B2 | 1/2006 | Drysen |
| 6,991,597 B2 | 1/2006 | Gellman et al. |
| 7,014,607 B2 | 3/2006 | Gellman |
| 7,025,063 B2 | 4/2006 | Snitkin et al. |
| 7,025,756 B2 | 4/2006 | Frazier et al. |
| 7,025,772 B2 | 4/2006 | Gellman et al. |
| 7,033,380 B2 | 4/2006 | Schwartz et al. |
| 7,037,255 B2 | 5/2006 | Inman et al. |
| 7,037,307 B2 | 5/2006 | Dennis |
| 7,037,324 B2 | 5/2006 | Martinek |
| 7,044,905 B2 | 5/2006 | Vidlund et al. |
| 7,048,682 B2 | 5/2006 | Neisz et al. |
| 7,052,495 B2 | 5/2006 | Smith |
| 7,056,333 B2 | 6/2006 | Walshe |
| 7,063,716 B2 | 6/2006 | Cunningham |
| 7,070,556 B2 | 7/2006 | Anderson et al. |
| 7,070,558 B2 | 7/2006 | Gellman et al. |
| 7,083,568 B2 | 8/2006 | Neisz et al. |
| 7,083,648 B2 | 8/2006 | Yu et al. |
| 7,087,065 B2 | 8/2006 | Ulmsten et al. |
| 7,094,199 B2 | 8/2006 | Petros et al. |
| 7,101,378 B2 | 9/2006 | Salameh et al. |
| 7,112,171 B2 | 9/2006 | Rocheleau et al. |
| 7,112,210 B2 | 9/2006 | Ulmsten et al. |
| 7,121,997 B2 | 10/2006 | Kammerer et al. |
| 7,131,943 B2 | 11/2006 | Kammerer |
| 7,131,944 B2 | 11/2006 | Jacquetin et al. |
| 7,163,506 B2 | 1/2007 | Grise |
| 7,198,597 B2 | 4/2007 | Siegel et al. |
| 7,204,801 B2 | 4/2007 | Grocela |
| 7,204,802 B2 | 4/2007 | De Leval et al. |
| RE39,626 E | 5/2007 | Tihon |
| D543,626 S | 5/2007 | Watschke et al. |
| 7,217,264 B2 | 5/2007 | Gobron et al. |
| 7,226,407 B2 | 6/2007 | Kammerer et al. |
| 7,226,408 B2 | 6/2007 | Harai et al. |
| 7,229,453 B2 | 6/2007 | Anderson et al. |
| 7,235,043 B2 | 6/2007 | Gellman et al. |
| 7,244,259 B2 | 7/2007 | Smith et al. |
| 7,261,723 B2 | 8/2007 | Smith et al. |
| 7,267,645 B2 | 9/2007 | Anderson et al. |
| 7,285,086 B2 | 10/2007 | Smith et al. |
| 7,288,063 B2 | 10/2007 | Petros et al. |
| 7,291,104 B2 | 11/2007 | Neisz et al. |
| 7,297,102 B2 | 11/2007 | Smith et al. |
| 7,303,525 B2 | 12/2007 | Watschke et al. |
| 7,326,213 B2 | 2/2008 | Benderev et al. |
| 7,338,432 B2 | 3/2008 | Valtchev |
| 7,347,812 B2 | 3/2008 | Mellier et al. |
| 7,347,813 B2 | 3/2008 | Claren et al. |
| 7,351,196 B2 | 4/2008 | Goldmann et al. |
| 7,351,197 B2 | 4/2008 | Montpetit et al. |
| 7,357,773 B2 | 4/2008 | Watschke |
| 7,364,541 B2 | 4/2008 | Chu et al. |
| 7,371,245 B2 | 5/2008 | Evans et al. |
| 7,387,634 B2 | 6/2008 | Benderev |
| 7,402,133 B2 | 7/2008 | Chu et al. |
| 7,404,819 B1 | 7/2008 | Darios et al. |
| 7,407,480 B2 | 8/2008 | Staskin et al. |
| 7,410,460 B2 | 8/2008 | Benderev |
| 7,413,540 B2 | 8/2008 | Gellman et al. |
| 7,422,557 B2 | 9/2008 | Arnal et al. |
| 7,500,945 B2 | 3/2009 | Cox et al. |
| 7,527,588 B2 | 5/2009 | Zaddem et al. |
| 7,588,598 B2 | 9/2009 | Delorme et al. |
| 7,611,454 B2 | 11/2009 | De Leval |
| 7,621,864 B2 | 11/2009 | Suslian et al. |
| 7,621,865 B2 | 11/2009 | Gellman et al. |
| 7,628,156 B2 | 12/2009 | Astani et al. |
| 7,658,743 B2 | 2/2010 | Ulmsten |
| 7,691,050 B2 | 4/2010 | Gellman et al. |
| 7,691,052 B2 | 4/2010 | Gellman et al. |
| 7,691,110 B2 | 4/2010 | Secrest et al. |
| 7,722,527 B2 | 5/2010 | Bouchier et al. |
| 7,771,345 B1 | 8/2010 | O'Donnell |
| 7,789,821 B2 | 9/2010 | Browning |
| 7,867,161 B2 | 1/2011 | Staskin et al. |
| 7,878,969 B2 | 2/2011 | Chu et al. |
| 7,896,848 B2 | 3/2011 | Charukhchian |
| 7,981,023 B2 | 7/2011 | Nowlin et al. |
| 7,988,615 B2 | 8/2011 | Anderson et al. |
| 8,007,430 B2 | 8/2011 | Browning |
| 8,033,983 B2 | 10/2011 | Chu et al. |
| 8,057,383 B2 | 11/2011 | Weiser et al. |
| 8,092,366 B2 | 1/2012 | Evans |
| 8,097,007 B2 | 1/2012 | Evans et al. |
| 8,123,671 B2 | 2/2012 | Evans |
| 8,206,280 B2 | 6/2012 | Evans et al. |
| 8,480,559 B2 | 7/2013 | Knapp et al. |
| 8,574,149 B2 | 11/2013 | Evans et al. |
| 2001/0000533 A1 | 4/2001 | Kovac |
| 2001/0008549 A1 | 7/2001 | Hashimoto |
| 2001/0010008 A1 | 7/2001 | Gellman et al. |
| 2001/0049467 A1 | 12/2001 | Lehe et al. |
| 2001/0051807 A1 | 12/2001 | Grafton |
| 2001/0053916 A1 | 12/2001 | Rioux |
| 2002/0007222 A1 | 1/2002 | Desai |
| 2002/0022841 A1 | 2/2002 | Kovac |
| 2002/0028980 A1 | 3/2002 | Thierfelder et al. |
| 2002/0052653 A1 | 5/2002 | Durgin |
| 2002/0055748 A1 | 5/2002 | Gellman et al. |
| 2002/0058959 A1 | 5/2002 | Gellman |
| 2002/0068948 A1 | 6/2002 | Stormby et al. |
| 2002/0072694 A1 | 6/2002 | Snitkin et al. |
| 2002/0077526 A1 | 6/2002 | Kammerer et al. |
| 2002/0078964 A1 | 6/2002 | Kovac et al. |
| 2002/0082619 A1 | 6/2002 | Cabak et al. |
| 2002/0091373 A1 | 7/2002 | Berger |
| 2002/0091391 A1 | 7/2002 | Cole et al. |
| 2002/0095181 A1 | 7/2002 | Beyar |
| 2002/0099258 A1 | 7/2002 | Staskin et al. |
| 2002/0099259 A1 | 7/2002 | Anderson et al. |
| 2002/0099260 A1 | 7/2002 | Suslian et al. |
| 2002/0107430 A1 | 8/2002 | Neisz et al. |
| 2002/0107525 A1 | 8/2002 | Harari et al. |
| 2002/0115906 A1 | 8/2002 | Miller |
| 2002/0128670 A1 | 9/2002 | Ulmsten et al. |
| 2002/0138025 A1 | 9/2002 | Gellman et al. |
| 2002/0147382 A1 | 10/2002 | Neisz et al. |
| 2002/0151762 A1 | 10/2002 | Rocheleau et al. |
| 2002/0151909 A1 | 10/2002 | Gellman et al. |
| 2002/0151910 A1 | 10/2002 | Gellman et al. |
| 2002/0156487 A1 | 10/2002 | Gellman et al. |

(56) References Cited

U.S. PATENT DOCUMENTS

| | | |
|---|---|---|
| 2002/0156488 A1 | 10/2002 | Gellman et al. |
| 2002/0156489 A1 | 10/2002 | Gellman et al. |
| 2002/0165566 A1 | 11/2002 | Ulmsten |
| 2002/0188169 A1 | 12/2002 | Kammerer et al. |
| 2002/0188301 A1 | 12/2002 | Dallara et al. |
| 2003/0004395 A1 | 1/2003 | Therin |
| 2003/0009181 A1 | 1/2003 | Gellman et al. |
| 2003/0023136 A1 | 1/2003 | Raz et al. |
| 2003/0023137 A1 | 1/2003 | Gellman |
| 2003/0023138 A1 | 1/2003 | Luscombe |
| 2003/0036676 A1 | 2/2003 | Scetbon |
| 2003/0036770 A1 | 2/2003 | Markman |
| 2003/0045774 A1 | 3/2003 | Staskin et al. |
| 2003/0045892 A1 | 3/2003 | Kaladelfos |
| 2003/0050530 A1 | 3/2003 | Neisz et al. |
| 2003/0065246 A1 | 4/2003 | Inman et al. |
| 2003/0065402 A1 | 4/2003 | Anderson et al. |
| 2003/0078604 A1 | 4/2003 | Walshe |
| 2003/0088250 A1 | 5/2003 | Colleran et al. |
| 2003/0130670 A1 | 7/2003 | Anderson et al. |
| 2003/0135239 A1 | 7/2003 | Gabriel et al. |
| 2003/0149440 A1 | 8/2003 | Kammerer et al. |
| 2003/0171644 A1 | 9/2003 | Anderson et al. |
| 2003/0176762 A1 | 9/2003 | Kammerer |
| 2003/0176875 A1 | 9/2003 | Anderson et al. |
| 2003/0191360 A1 | 10/2003 | Browning |
| 2003/0199732 A1 | 10/2003 | Suslian et al. |
| 2003/0212305 A1 | 11/2003 | Anderson et al. |
| 2003/0216693 A1 | 11/2003 | Mickley |
| 2003/0220538 A1 | 11/2003 | Jacquetin |
| 2003/0225424 A1 | 12/2003 | Benderev |
| 2003/0229350 A1 | 12/2003 | Kay |
| 2004/0006353 A1 | 1/2004 | Bosley et al. |
| 2004/0015048 A1 | 1/2004 | Neisz et al. |
| 2004/0015057 A1 | 1/2004 | Rocheleau et al. |
| 2004/0039246 A1 | 2/2004 | Gellman et al. |
| 2004/0039453 A1 | 2/2004 | Anderson et al. |
| 2004/0040159 A1 | 3/2004 | Fossella |
| 2004/0044364 A1 | 3/2004 | DeVries et al. |
| 2004/0059336 A1 | 3/2004 | Lombardo et al. |
| 2004/0068159 A1 | 4/2004 | Neisz et al. |
| 2004/0073219 A1 | 4/2004 | Skiba et al. |
| 2004/0073234 A1 | 4/2004 | Chu et al. |
| 2004/0087970 A1 | 5/2004 | Chu et al. |
| 2004/0087980 A1 | 5/2004 | Ford et al. |
| 2004/0097974 A1 | 5/2004 | De Leval |
| 2004/0097975 A1 | 5/2004 | Rose |
| 2004/0106845 A1 | 6/2004 | Anderson et al. |
| 2004/0106847 A1 | 6/2004 | Benderev |
| 2004/0106925 A1 | 6/2004 | Culbert |
| 2004/0111895 A1 | 6/2004 | Huang |
| 2004/0116774 A1 | 6/2004 | Migliari |
| 2004/0116944 A1 | 6/2004 | Chu et al. |
| 2004/0122474 A1 | 6/2004 | Gellman et al. |
| 2004/0133217 A1 | 7/2004 | Watschke |
| 2004/0144395 A1 | 7/2004 | Evans et al. |
| 2004/0153008 A1 | 8/2004 | Sharf et al. |
| 2004/0153074 A1 | 8/2004 | Bojarski et al. |
| 2004/0153103 A1 | 8/2004 | Schwartz et al. |
| 2004/0172048 A1 | 9/2004 | Browning |
| 2004/0209538 A1 | 10/2004 | Klinge et al. |
| 2004/0220595 A1 | 11/2004 | Frazier et al. |
| 2004/0225181 A1 | 11/2004 | Chu et al. |
| 2004/0225301 A1 | 11/2004 | Roop et al. |
| 2004/0230206 A1 | 11/2004 | Gellman et al. |
| 2004/0230207 A1 | 11/2004 | Gellman et al. |
| 2004/0231678 A1 | 11/2004 | Fierro |
| 2004/0249240 A1 | 12/2004 | Goldmann et al. |
| 2004/0249396 A1 | 12/2004 | Lund et al. |
| 2004/0249473 A1 | 12/2004 | Delorme et al. |
| 2004/0254609 A1 | 12/2004 | Esplin |
| 2004/0267088 A1 | 12/2004 | Kammerer |
| 2005/0004576 A1 | 1/2005 | Benderev |
| 2005/0021086 A1 | 1/2005 | De Leval |
| 2005/0028380 A1 | 2/2005 | Fossella |
| 2005/0033365 A1 | 2/2005 | Courage |
| 2005/0038370 A1 | 2/2005 | Kuth et al. |
| 2005/0043580 A1 | 2/2005 | Watschke et al. |
| 2005/0065395 A1 | 3/2005 | Mellier |
| 2005/0070829 A1 | 3/2005 | Therin et al. |
| 2005/0075654 A1 | 4/2005 | Kelleher |
| 2005/0075660 A1 | 4/2005 | Chu et al. |
| 2005/0085831 A1 | 4/2005 | Rioux |
| 2005/0090706 A1 | 4/2005 | Gellman et al. |
| 2005/0090841 A1 | 4/2005 | Morrison |
| 2005/0101834 A1 | 5/2005 | Merade |
| 2005/0101973 A1 | 5/2005 | Smith et al. |
| 2005/0107660 A1 | 5/2005 | Valtchev |
| 2005/0113845 A1 | 5/2005 | Griego et al. |
| 2005/0131274 A1 | 6/2005 | Suslian et al. |
| 2005/0131391 A1 | 6/2005 | Chu |
| 2005/0131392 A1 | 6/2005 | Chu et al. |
| 2005/0131393 A1 | 6/2005 | Chu et al. |
| 2005/0131429 A1 | 6/2005 | Ho et al. |
| 2005/0143618 A1 | 6/2005 | Anderson et al. |
| 2005/0148813 A1 | 7/2005 | Claren et al. |
| 2005/0149122 A1 | 7/2005 | McDevitt et al. |
| 2005/0177022 A1 | 8/2005 | Chu et al. |
| 2005/0228413 A1 | 10/2005 | Binmoeller et al. |
| 2005/0234291 A1 | 10/2005 | Gingras |
| 2005/0240076 A1 | 10/2005 | Neisz et al. |
| 2005/0251083 A1 | 11/2005 | Carr-Brendel et al. |
| 2005/0251159 A1 | 11/2005 | Ewers et al. |
| 2005/0251177 A1 | 11/2005 | Saadat et al. |
| 2005/0251202 A1 | 11/2005 | Ewers et al. |
| 2005/0251210 A1 | 11/2005 | Westra et al. |
| 2005/0256366 A1 | 11/2005 | Chu |
| 2005/0256530 A1 | 11/2005 | Petros |
| 2005/0261545 A1 | 11/2005 | Gellman et al. |
| 2005/0273138 A1 | 12/2005 | To et al. |
| 2005/0277806 A1 | 12/2005 | Cristalli |
| 2005/0277807 A1 | 12/2005 | MacLean et al. |
| 2005/0277966 A1 | 12/2005 | Ewers et al. |
| 2005/0277981 A1 | 12/2005 | Maahs et al. |
| 2005/0283040 A1 | 12/2005 | Greenhalgh |
| 2005/0288689 A1 | 12/2005 | Kammerer et al. |
| 2006/0015001 A1 | 1/2006 | Staskin et al. |
| 2006/0015069 A1 | 1/2006 | Evans et al. |
| 2006/0025649 A1 | 2/2006 | Smith et al. |
| 2006/0041185 A1 | 2/2006 | Browning |
| 2006/0058574 A1 | 3/2006 | Priewe et al. |
| 2006/0058575 A1 | 3/2006 | Zaddem et al. |
| 2006/0058578 A1 | 3/2006 | Browning |
| 2006/0059693 A1 | 3/2006 | Fossella |
| 2006/0059695 A1 | 3/2006 | Levine et al. |
| 2006/0063968 A1 | 3/2006 | Anderson et al. |
| 2006/0089524 A1 | 4/2006 | Chu |
| 2006/0089525 A1 | 4/2006 | Mamo et al. |
| 2006/0100628 A1 | 5/2006 | Martinek |
| 2006/0106277 A1 | 5/2006 | Romero Maroto |
| 2006/0116719 A1 | 6/2006 | Martinek |
| 2006/0122457 A1 | 6/2006 | Kovac et al. |
| 2006/0130848 A1 | 6/2006 | Carey |
| 2006/0134159 A1 | 6/2006 | Nicita |
| 2006/0149123 A1 | 7/2006 | Vidlund et al. |
| 2006/0173237 A1 | 8/2006 | Jacquetin |
| 2006/0173471 A1 | 8/2006 | Carr, Jr. et al. |
| 2006/0173864 A1 | 8/2006 | Dart et al. |
| 2006/0183966 A1 | 8/2006 | Neisz et al. |
| 2006/0184234 A1 | 8/2006 | Frazier et al. |
| 2006/0195007 A1 | 8/2006 | Anderson et al. |
| 2006/0195010 A1 | 8/2006 | Arnal et al. |
| 2006/0195011 A1 | 8/2006 | Arnal et al. |
| 2006/0195013 A1 | 8/2006 | Gellman et al. |
| 2006/0196137 A1 | 9/2006 | Brenzel et al. |
| 2006/0199994 A1 | 9/2006 | Inman et al. |
| 2006/0199996 A1 | 9/2006 | Caraballo et al. |
| 2006/0201519 A1 | 9/2006 | Frazier et al. |
| 2006/0205995 A1 | 9/2006 | Browning |
| 2006/0205998 A1 | 9/2006 | Li et al. |
| 2006/0207606 A1 | 9/2006 | Roue et al. |
| 2006/0217762 A1 | 9/2006 | Maahs et al. |
| 2006/0229493 A1 | 10/2006 | Weiser et al. |
| 2006/0229596 A1 | 10/2006 | Weiser et al. |

(56) References Cited

U.S. PATENT DOCUMENTS

| | | |
|---|---|---|
| 2006/0235262 A1 | 10/2006 | Arnal et al. |
| 2006/0235447 A1 | 10/2006 | Walshe |
| 2006/0247490 A1 | 11/2006 | Merade et al. |
| 2006/0252980 A1 | 11/2006 | Arnal et al. |
| 2006/0258897 A1 | 11/2006 | Petros et al. |
| 2006/0258898 A1 | 11/2006 | Montpetit et al. |
| 2006/0260618 A1 | 11/2006 | Hodroff et al. |
| 2006/0264698 A1 | 11/2006 | Kondonis et al. |
| 2006/0287571 A1 | 12/2006 | Gozzi et al. |
| 2007/0010830 A1 | 1/2007 | Gellman et al. |
| 2007/0015957 A1 | 1/2007 | Li |
| 2007/0021649 A1 | 1/2007 | Nowlin et al. |
| 2007/0021650 A1 | 1/2007 | Rocheleau et al. |
| 2007/0021686 A1 | 1/2007 | Gellman et al. |
| 2007/0032695 A1 | 2/2007 | Weiser |
| 2007/0038017 A1 | 2/2007 | Chu |
| 2007/0038018 A1 | 2/2007 | Chu |
| 2007/0043255 A1 | 2/2007 | O'Donnell |
| 2007/0043336 A1 | 2/2007 | Griffin et al. |
| 2007/0049790 A1 | 3/2007 | Wagner et al. |
| 2007/0049791 A1 | 3/2007 | Merade et al. |
| 2007/0055094 A1 | 3/2007 | Chen |
| 2007/0055095 A1 | 3/2007 | Chu et al. |
| 2007/0060788 A1 | 3/2007 | Gellman |
| 2007/0062541 A1 | 3/2007 | Zhou et al. |
| 2007/0068538 A1 | 3/2007 | Anderson et al. |
| 2007/0078295 A1 | 4/2007 | Landgrebe |
| 2007/0088390 A1 | 4/2007 | Paz et al. |
| 2007/0089750 A1 | 4/2007 | Astani et al. |
| 2007/0089751 A1 | 4/2007 | Astani et al. |
| 2007/0123746 A1 | 5/2007 | MacLean |
| 2007/0142698 A1 | 6/2007 | Bourne et al. |
| 2007/0156012 A1 | 7/2007 | Tracey et al. |
| 2007/0161849 A1 | 7/2007 | Goldberg |
| 2007/0203429 A1 | 8/2007 | Ziv |
| 2007/0225546 A1 | 9/2007 | Anderson et al. |
| 2007/0299299 A1 | 12/2007 | Rosenblatt |
| 2007/0299300 A1 | 12/2007 | Smith et al. |
| 2008/0004490 A1 | 1/2008 | Bosley et al. |
| 2008/0009665 A1 | 1/2008 | Merade et al. |
| 2008/0009667 A1 | 1/2008 | Longhini et al. |
| 2008/0009888 A1 | 1/2008 | Ewers et al. |
| 2008/0039678 A1 | 2/2008 | Montpetit et al. |
| 2008/0045782 A1 | 2/2008 | Jimenez |
| 2008/0082121 A1 | 4/2008 | Chu |
| 2008/0097329 A1 | 4/2008 | Hodroff et al. |
| 2008/0132753 A1 | 6/2008 | Goddard |
| 2008/0269547 A1 | 10/2008 | Hortenstine |
| 2008/0281148 A1 | 11/2008 | Evans et al. |
| 2008/0300607 A1 | 12/2008 | Meade et al. |
| 2009/0105743 A1 | 4/2009 | Chu |
| 2009/0137862 A1 | 5/2009 | Evans et al. |
| 2009/0149700 A1 | 6/2009 | Garcia et al. |
| 2009/0221868 A1 | 9/2009 | Evans |
| 2009/0306464 A1 | 12/2009 | Griguol |
| 2009/0318752 A1 | 12/2009 | Evans et al. |
| 2010/0010501 A2 | 1/2010 | Meade et al. |
| 2010/0030015 A1 | 2/2010 | Delorme et al. |
| 2010/0056856 A1 | 3/2010 | Suslian et al. |
| 2010/0197999 A1 | 8/2010 | Deegan et al. |
| 2010/0217069 A1 | 8/2010 | Meade et al. |
| 2010/0234679 A1 | 9/2010 | Evans |
| 2010/0234681 A1 | 9/2010 | Knapp et al. |
| 2010/0241105 A1 | 9/2010 | Meade et al. |
| 2011/0082328 A1 | 4/2011 | Gozzi et al. |
| 2011/0105833 A1 | 5/2011 | Gozzi et al. |
| 2011/0124954 A1 | 5/2011 | Ogdahl et al. |
| 2011/0282133 A1 | 11/2011 | Anderson et al. |
| 2012/0029488 A1 | 2/2012 | Chu |
| 2012/0116154 A1 | 5/2012 | Evans et al. |
| 2012/0253110 A1 | 10/2012 | Evans et al. |
| 2014/0058193 A1 | 2/2014 | Evans et al. |

FOREIGN PATENT DOCUMENTS

| | | |
|---|---|---|
| DE | 3223153 C1 | 8/1983 |
| DE | 4220283 A1 | 12/1993 |
| DE | 4334419 A1 | 4/1995 |
| DE | 19544162 C1 | 4/1997 |
| DE | 10138950 A1 | 2/2003 |
| DE | 102 11 360 A1 | 10/2003 |
| DE | 10245076 A1 | 4/2004 |
| EP | 0437481 A1 | 7/1991 |
| EP | 0537769 A1 | 4/1993 |
| EP | 0556313 | 8/1993 |
| EP | 0557964 A1 | 9/1993 |
| EP | 0598976 A2 | 6/1994 |
| EP | 0619984 A1 | 10/1994 |
| EP | 0648474 A1 | 4/1995 |
| EP | 0668056 A1 | 8/1995 |
| EP | 0692225 A2 | 1/1996 |
| EP | 0740925 | 11/1996 |
| EP | 0745351 | 12/1996 |
| EP | 0774240 A1 | 5/1997 |
| EP | 0778749 | 6/1997 |
| EP | 0854691 | 7/1998 |
| EP | 0913162 A1 | 5/1999 |
| EP | 0941712 A1 | 9/1999 |
| EP | 0983033 B1 | 3/2000 |
| EP | 1018980 B1 | 7/2000 |
| EP | 1093758 | 4/2001 |
| EP | 1151722 | 11/2001 |
| EP | 1159920 A2 | 12/2001 |
| EP | 1159921 | 12/2001 |
| EP | 1239793 B1 | 9/2002 |
| EP | 1239795 B1 | 9/2002 |
| EP | 1342450 A1 | 9/2003 |
| EP | 1342454 A1 | 9/2003 |
| EP | 1399082 B1 | 3/2004 |
| EP | 1417934 A2 | 5/2004 |
| EP | 1487377 A1 | 12/2004 |
| EP | 1534154 | 6/2005 |
| EP | 1549245 B1 | 7/2005 |
| EP | 1600118 A1 | 11/2005 |
| EP | 1609439 A1 | 12/2005 |
| EP | 1610714 A2 | 1/2006 |
| EP | 1688105 A2 | 8/2006 |
| EP | 1909672 A2 | 4/2008 |
| EP | 1545285 B1 | 11/2010 |
| EP | 1948073 A4 | 3/2011 |
| FR | 2712177 A1 | 5/1995 |
| FR | 2785521 | 5/2000 |
| FR | 0102120 | 1/2002 |
| FR | 2852817 A1 | 10/2004 |
| FR | 2859624 A1 | 3/2005 |
| FR | 2859901 A1 | 3/2005 |
| GB | 2382993 B | 6/2003 |
| JP | 03070567 A | 3/1991 |
| JP | 05161655 A | 6/1993 |
| JP | 11221221 A | 8/1999 |
| JP | 2002503510 A | 2/2002 |
| JP | 2002143290 A | 5/2002 |
| JP | 2003501144 A | 1/2003 |
| JP | 2003225240 A | 8/2003 |
| JP | 2005505313 A | 2/2005 |
| JP | 2005534422 A | 11/2005 |
| JP | 4452180 B2 | 4/2010 |
| SE | 503271 C2 | 4/1996 |
| WO | 9003766 | 4/1990 |
| WO | 9003766 A1 | 4/1990 |
| WO | 9208412 A1 | 5/1992 |
| WO | 9310731 A1 | 6/1993 |
| WO | 9315690 A2 | 8/1993 |
| WO | 9603091 A1 | 2/1996 |
| WO | 9606567 | 3/1996 |
| WO | 9606567 A1 | 3/1996 |
| WO | 9606597 A1 | 3/1996 |
| WO | 9607355 A1 | 3/1996 |
| WO | 9608587 A1 | 3/1996 |
| WO | 9640307 A1 | 12/1996 |
| WO | 9713465 | 4/1997 |
| WO | 9713465 A1 | 4/1997 |

(56) References Cited

FOREIGN PATENT DOCUMENTS

| | | |
|---|---|---|
| WO | 9716121 | 5/1997 |
| WO | 9743982 A1 | 11/1997 |
| WO | 9831301 A1 | 7/1998 |
| WO | 9835632 | 8/1998 |
| WO | 9835632 A1 | 8/1998 |
| WO | 9922873 A1 | 5/1999 |
| WO | 9934744 A1 | 7/1999 |
| WO | 9942041 A1 | 8/1999 |
| WO | 9959477 A1 | 11/1999 |
| WO | 0018325 | 4/2000 |
| WO | 0027304 | 5/2000 |
| WO | 0027304 A1 | 5/2000 |
| WO | 0040158 A2 | 7/2000 |
| WO | 0064370 A1 | 11/2000 |
| WO | 0066030 | 11/2000 |
| WO | 0074594 | 12/2000 |
| WO | 0074594 A1 | 12/2000 |
| WO | 0074613 | 12/2000 |
| WO | 0074613 A1 | 12/2000 |
| WO | 0074633 | 12/2000 |
| WO | 0106951 A1 | 2/2001 |
| WO | 0130246 | 5/2001 |
| WO | 0147438 A1 | 7/2001 |
| WO | 0152750 | 7/2001 |
| WO | 0180774 A1 | 11/2001 |
| WO | 0193656 A2 | 12/2001 |
| WO | 0202031 | 1/2002 |
| WO | 0202031 A1 | 1/2002 |
| WO | 0219945 A2 | 3/2002 |
| WO | 0219946 | 3/2002 |
| WO | 0226108 | 4/2002 |
| WO | 0228312 | 4/2002 |
| WO | 0228312 A1 | 4/2002 |
| WO | 0228315 | 4/2002 |
| WO | 0232284 A2 | 4/2002 |
| WO | 0238079 A2 | 5/2002 |
| WO | 0239890 A2 | 5/2002 |
| WO | 0239914 | 5/2002 |
| WO | 02058562 | 8/2002 |
| WO | 02058562 A1 | 8/2002 |
| WO | 02058563 A1 | 8/2002 |
| WO | 02058564 | 8/2002 |
| WO | 02058565 | 8/2002 |
| WO | 02058565 A2 | 8/2002 |
| WO | 02062237 | 8/2002 |
| WO | 02065921 | 8/2002 |
| WO | 02065922 | 8/2002 |
| WO | 02065923 | 8/2002 |
| WO | 02065923 A1 | 8/2002 |
| WO | 02069781 A2 | 9/2002 |
| WO | 02071931 | 9/2002 |
| WO | 02071931 A1 | 9/2002 |
| WO | 02078548 A1 | 10/2002 |
| WO | 02098322 | 12/2002 |
| WO | 02098322 A1 | 12/2002 |
| WO | 03002027 | 1/2003 |
| WO | 03002027 A1 | 1/2003 |
| WO | 03013369 | 2/2003 |
| WO | 03028585 A2 | 4/2003 |
| WO | 03037215 A2 | 5/2003 |
| WO | 03053252 A1 | 7/2003 |
| WO | 03068107 | 8/2003 |
| WO | 03068107 A1 | 8/2003 |
| WO | 03073960 A1 | 9/2003 |
| WO | 03075792 | 9/2003 |
| WO | 03086205 A2 | 10/2003 |
| WO | 03092546 | 11/2003 |
| WO | 03096928 | 11/2003 |
| WO | 03096929 A1 | 11/2003 |
| WO | 03096930 | 11/2003 |
| WO | 03096930 A1 | 11/2003 |
| WO | 03101344 A1 | 12/2003 |
| WO | 2004004600 A1 | 1/2004 |
| WO | 2004008977 A1 | 1/2004 |
| WO | 2004012579 A2 | 2/2004 |
| WO | 2004012626 A1 | 2/2004 |
| WO | 2004016196 A2 | 2/2004 |
| WO | 2004017862 A2 | 3/2004 |
| WO | 2004019786 | 3/2004 |
| WO | 2004034912 A1 | 4/2004 |
| WO | 2004056273 A1 | 7/2004 |
| WO | 2004086983 A1 | 10/2004 |
| WO | 2004091442 A2 | 10/2004 |
| WO | 2004098461 A2 | 11/2004 |
| WO | 2005037132 A2 | 4/2005 |
| WO | 2005087153 A2 | 9/2005 |
| WO | 2005094741 A1 | 10/2005 |
| WO | 2005110273 A1 | 11/2005 |
| WO | 2005110274 A2 | 11/2005 |
| WO | 2005112842 A1 | 12/2005 |
| WO | 2005122954 A1 | 12/2005 |
| WO | 2006040307 A1 | 4/2006 |
| WO | 2006045042 A1 | 4/2006 |
| WO | 2006046950 A1 | 5/2006 |
| WO | 2006069078 A2 | 6/2006 |
| WO | 2006081545 | 8/2006 |
| WO | 2006084165 A2 | 8/2006 |
| WO | 2006084166 A2 | 8/2006 |
| WO | 2006108145 A1 | 10/2006 |
| WO | 2006108964 A2 | 10/2006 |
| WO | 2007013465 A1 | 2/2007 |
| WO | 2007059199 A2 | 5/2007 |
| WO | 2007087190 A2 | 8/2007 |
| WO | 2007097994 A2 | 8/2007 |
| WO | 2007149348 A2 | 12/2007 |
| WO | 2008033950 A2 | 3/2008 |
| WO | 2008065467 A1 | 6/2008 |
| WO | 2009064866 A1 | 5/2009 |

OTHER PUBLICATIONS

Shands Healthcare, "Bladder neck is elevated by stitching it and the urethra to anterior pubic bone," Copyright 1997-2011, printed Nov. 3, 2010,<http://www.shands.org/health/imagepages/17202.htm>.

Silver, Richard I., et al., "Staged closure of the pelvis in cloacal exstrophy: first description of a new approach," The Journal of Urology, Jan. 1999, vol. 161, pp. 263-266.

Stanton, Stuart L.; "Suprapubic Approaches for Stress Incontinence in Women"; Journal of the American Geriatrics Society, vol. 38, No. 3, pp. 348-351, Mar. 1990.

Staskin, David R., Choe, Jong M., Breslin, David S.; "The Gore-Tex sling procedure for female sphincteric incontinence: indications, technique, and results"; World J. Urol.; vol. 15, pp. 295-299, 1997.

Sussman, J.S., et al., "A Comparison of Methods of Repairing the Symphysis Pubis in Bladder Exstrophy by Tensile Testing," Brit. J. Urol., 79: 979-984, 1997.

Ulmsten, U. et al., "An Ambulatory Surgical Procedure Under Local Anesthesia for Treatment of Female Urinary Incontinence," Int Urogynecol J (1996) 7:81-86.

U.S. Appl. No. 10/633,254, filed Aug. 1, 2003 Advisory Action dated Aug. 26, 2008.

U.S. Appl. No. 10/633,254, filed Aug. 1, 2003 Decision on Appeal dated Jul. 20, 2011.

U.S. Appl. No. 10/633,254, filed Aug. 1, 2003 Final Office Action dated Jun. 18, 2008.

U.S. Appl. No. 10/633,254, filed Aug. 1, 2003 Non-Final Office Action dated Jan. 29, 2007.

U.S. Appl. No. 10/633,254, filed Aug. 1, 2003 Non-Final Office Action dated Nov. 15, 2005.

U.S. Appl. No. 10/633,254, filed Aug. 1, 2003 Non-Final Office Action dated Sep. 18, 2007.

U.S. Appl. No. 10/633,254, filed Aug. 1, 2003 Notice of Allowance dated Oct. 11, 2011.

U.S. Appl. No. 11/993,003, filed Jan. 22, 2008 Examiner's Answer dated Nov. 30, 2011.

U.S. Appl. No. 11/993,003, filed Jan. 22, 2008 Non-Final Office Action dated Jul. 20, 2011.

U.S. Appl. No. 11/993,089, filed Jun. 9, 2010 Non-Final Office Action dated Aug. 27, 2012.

(56) References Cited

OTHER PUBLICATIONS

U.S. Appl. No. 11/993,375, filed Feb. 6, 2009 Non-Final Office Action dated May 10, 2011.
U.S. Appl. No. 11/993,003, filed Jan. 22, 2008 Advisory Action dated Feb. 8, 2011.
U.S. Appl. No. 11/993,003, filed Jan. 22, 2008 Final Office Action dated Dec. 10, 2010.
U.S. Appl. No. 11/993,003, filed Jan. 22, 2008 Non-Final Office Action dated Jul. 14, 2010.
U.S. Appl. No. 12/159,589, filed Aug. 15, 2008 Examiner's Answer dated Nov. 9, 2011.
U.S. Appl. No. 12/159,589, filed Aug. 15, 2008 Final Office Action dated May 12, 2011.
U.S. Appl. No. 12/159,589, filed Aug. 15, 2008 Non-Final Office Action dated Dec. 10, 2010.
U.S. Appl. No. 12/159,589, filed Aug. 15, 2008 Non-Final Office Action dated Jul. 12, 2010.
U.S. Appl. No. 12/159,589, filed Aug. 15, 2008 Notice of Panel Decision dated Aug. 29, 2011.
U.S. Appl. No. 12/269,749, filed Nov. 12, 2008 Non-Final Office Action dated Sep. 14, 2011.
U.S. Appl. No. 12/269,749, filed Nov. 12, 2008 Notice of Allowance dated Mar. 16, 2012.
U.S. Appl. No. 12/282,641, filed Dec. 4, 2008 Non-Final Office Action dated Dec. 8, 2011.
U.S. Appl. No. 12/282,641, filed Dec. 4, 2008 Non-Final Office Action dated Jul. 12, 2012.
U.S. Appl. No. 12/441,123, filed May 24, 2010 Advisory Action dated Dec. 7, 2012.
U.S. Appl. No. 12/441,123, filed May 24, 2010 Final Office Action dated Sep. 14, 2012.
U.S. Appl. No. 12/441,123, filed May 24, 2010 Non-Final Office Action dated Apr. 9, 2012.
U.S. Appl. No. 13/524,408, filed Jun. 15, 2012 Non-Final Office Action dated Mar. 7, 2013.
Wahle, Gregory R. et al., "Vaginal Surgery for Stress Urinary Incontinence," Urology, vol. 43, No. 4, pp. 416-419, Apr. 1994.
Wall, LL, et al., Use of a pedicled rectus abdominus muscle flap sling in the treatment of complicated stress urinary incontinence. Am J Obstet Gynecol. Dec. 1996;175(6):1460-4; Discussion 1464-6.
Walters, Mark D., et al., "Anterior vaginal wall prolapse: Innovative surgical approaches," Cleveland Clinic Journal of Medicine, Dec. 2005, 72:4 S20-S27.
Yan, A., et al, "Cystocele repair by a synthetic vaginal mesh secured anteriorly through the obturator foramen," Eur J Obstet Gynecol Reprod Biol, Jul. 15, 2004;115(1):90-4.
Zimmern, Philippe, et al., "A prospective evaluation of four-corner bladder neck suspension for grade II/III cystocele repair," Urodynamics Soc. Symp. Abstracts, p. 231 (1990).
AU 2006332514 filed Dec. 28, 2006 First Examiner's Report dated Oct. 4, 2011.
AU 2006332514 filed Dec. 28, 2006 Second Examiner's Report dated Jul. 5, 2012.
Bard (Article), "Avaulta™ BioSynthetic Support System," http://www.crbard.com/news/innovations/Avaulta.cfm (2007).
Bard (Article), "AVAULT™ Bio-Synthetic Support System 'Anterior and Posterior Posterior Pelvic Floor Defect Repair with the Avaulta™ Bio-synthetic Support system,'" http://www.bardmdu.com/products/loadProduct.aspx?prodID=280&bUnitID=3 (2007).
Bard (Article), "PelviLace® TO Trans-Obturator BioUrethral Support System," http://www.bardurological.com/products/loadproduct.aspx?prodID=277 (2008).
Bard (Article), "Uretex® TO—Trans-Obturator Urethral Support System 'Not all Mesh is created equal,'" Copyright 1997-2004, <http://www.barduroloqical.com/products/loadproductaspx?prodID=186>.
Bard Photo Library "Uretex® Mesh," printed Jul. 12, 2006; http://www.bardurological.com/products/product_photoLibrary.aspx?prodID=185&photoID 32 269.
Bard Photo Library, Avaulta™ "Posterior BioSynthetic Support System", Copyright 1997-2008; printed Oct. 23, 2008; http://www.bardurological.com/products/product_photolibrary.aspx?prodID=281&photoID=326>.
Bard Photo Library, Uretex® Mesh in the Anatomy—printed Jul. 12, 2006 <http://www.bardurological.com/products/product_photoLibrary.aspx?prodID=185&photoID=270>.
Bard Photo Library, Hook Introducer 2 printed Jul. 12, 2006 <http://www.bardurological.com/products/product_photoLibrary.aspx?prodID=186&photoID=344>.
Bard Photo Library, Hook Introducer printed Jul. 12, 2006 http://www.bardurological.com/products/product_photoLibrary.aspx?prodID=186&photoID=343.
Bard Photo Library, Pelvic Diagram 1 (photo id 282) printed Jul. 12, 2006 http://www.bardurological.com/products/product_photoLibrary.aspx?prodID=186&photoID=282.
Bard Photo Library, Pelvic Diagram 2 (photo id 283) printed Jul. 12, 2006 http://www.bardurological.com/products/product_photoLibrary.aspx?prodID=186&photoID=283.
Bard Photo Library, Pelvic Diagram 3 (photo id 284) printed Jul. 12, 2006 http://www.bardurological.com/products/product_photoLibrary.aspx?prodID=186&photoID=284.
Bard Photo Library, Pelvic Diagram 4 (photo id 285) printed Jul. 12, 2006 http://www.bardurological.com/products/product_photoLibrary.aspx?prodID=186&photoID=285.
Bard Photo Library, Surgical Technique (photo id 336) printed Jul. 12, 2006 http://www.bardurological.com/products/product_photoLibrary.aspx?prodID=186&photoID=336.
Bard Photo Library, Surgical Techniques (photo id 337) printed on Jul. 12, 2006 http://www.bardurological.com/products/product_photoLibrary.aspx?prodID=186&photoID=337.
Bard Photo Library, Surgical Techniques (photo id 338) printed Jul. 12, 2006 http://www.bardurological.com/products/product_photoLibrary.aspx?prodID=186&photoID=338.
Bard Photo Library, Surgical Techniques (photo id 339) printed Jul. 12, 2006 http://www.bardurological.com/products/product_photoLibrary.aspx?prodID=186&photoID=339.
Bard Photo Library, Surgical Techniques (photo id 340) printed Jul. 12, 2006 http://www.bardurological.com/products/product_photoLibrary.aspx?prodID=186&photoID=340.
Bard Photo Library, Surgical Techniques (photo id 341) printed Jul. 12, 2006 http://www.bardurological.com/products/product_photoLibrary.aspx?prodID=186&photoID=341.
Bard Photo Library, Surgical Techniques (photo id 345) printed Jul. 12, 2006 http://www.bardurological.com/products/product_photoLibrary.aspx?prodID=186&photoID=345.
Bard Photo Library, Uretex T.O. Transobturator Urethral Support System printed Jul. 12, 2006 <http://www.bardurological.com/products/product_photoLibrary.aspx?productID=186&photoID=266>.
Bard Photo Library, Uretex® TO Trans-Obturator Urethral Support System dated Oct. 23, 2008<http://www.bardurological.com/products/product_photoLibrary.aspx?prodID=186&photoID=204&bUnitID=2>.
Bard Photo Library, Urethral Mesh printed Jul. 12, 2006 <http://www.bardurological.com/products/product_photoLibrary.aspx?prodID=185&photoID=271>.
Bard, "Avaulta™ Anterior BioSynthectic Support System," Copyright 2006-2011, http://www.bardnordic.com/main/product.asp?.sectionTypeID=2&sectionID=6&productID=247.
Bard, "Uretex® Self-Anchoring Urethral Support System—FAQ," printed Jul. 12, 2006; <http://www.bardurological.com/products/product_faq.aspx?prodID=185>.
Bryans, Fred E. "Marlex gauze hammock sling operation with Cooper's ligament attachment in the management of recurrent urinary stress incontinence." American Journal of Obstetrics and Gynecology, vol. 133, No. 3, Feb. 1979.
Burch, John C., "Urethrovaginal fixation to Cooper's ligament for correction of stress incontinence, cystocele, and prolapse," Am. J. Obst. & Gyne, 281-290 (1961).
Burch, John C.; "Urethrovaginal fixation to Cooper's ligament for correction of stress incontinence, cystocele, and prolapse." American Journal of Obstetrics & Gynecology, vol. 31, No. 2, Feb. 1961, pp. 281-290.

(56) References Cited

OTHER PUBLICATIONS

Choe, JM, "Preventing urethral obstruction using the 6-point fixation and weight-adjusted spacing nomogram during sling surgery," Int Urogynecol J Pelvic Floor Dysfunct, 2001;12(2):122-8.
Choe, Jong M., Staskin, David R.; "Gore-Tex Patch Sling: 7 Years Later"; Adult Urology, 54(4), pp. 641-646, 1999.
CN 200880115957.3 filed May 12, 2010 Office Action dated Apr. 28, 2012.
CN 200880115957.3 filed May 12, 2010 Office Action dated Dec. 12, 2012.
Collinet, P., et al., "Cure de cystocele par plastron vaginal," J Gynecol Obstet Biol Reprod, 29:197-201 (2000).
Cook Medical, Needle Suspension Product Pages, <<http://www.cookmedical.com>>, last accessed Aug. 13, 2008.
Cook; Urogynecology; Product Technical Datasheet and Order form. 1996.
Cosson, M., et al., "Cure of cystocele with vaginal patch," Prog Urol. Apr. 2001;11(2):340-6.
Cosson, M., et al., "The vaginal patch plastron for vaginal cure of cystocele. Preliminary results for 47 patients," Eur J Obstet Gynecol Reprod Giol. Mar. 2001;95(1):73-80.
Cosson, Michel, et al., "Cure de cystocele par plastron vaginal," Progres en Urologie, 11:340-346 (2001).
Cruikshank, Stephen H., et al., "Anterior vaginal wall culdeplasty at vaginal hysterectomy to prevent posthysterectomy anterior vaginal wall prolapse," Am. J. Obstet. Gynecol., 1863-1872 (1996).
De Leval J., "Novel surgical technique for the treatment of female stress urinary incontinence: transobturator vaginal tape inside-out," Eur Urol. Dec. 2003;44(6):724-30.
Delorme, E., "Transobturator urethral suspension: mini-invasive procedure in the treatment of stress urinary incontinence in women," Prog Urol. Dec. 2001;11(6):1306-13.
Delorme, E., et al., "Transobturator tape (Uratape). A new minimally invasive method in the treatment of urinary incontinence in women," Prog Urol. Sep. 2003;13(4):656-9.
Delorme, Emmanuel., "Transobturator urethral suspension: mini-invasive procedure in the treatment of stress urinary incontinence in women," Progress in Urology, 11(6):1306-13, Dec. 2001.
Di Benedetto, V., et al., "Transurethral Puncture of Ureterocele Associated With Single Collecting System in Neonates," J. Ped. Surg., 32:1325-1327, 1997.
Dmochowski et al., "Biocompatibility Assessment of Synthetic Sling Materials for Female Stress Urinary Incontinence," The Journal of Urology, vol. 178, Issue 4, pp. 1171-1181, Oct. 2007.
Dmochowski et al., "Erosion of Woven Polyester Pubovaginal Sling," The Journal of Urology, vol. 162, Issue 6, pp. 2070-2072, Dec. 1999.
Dmochowski, R., et al., "The Protegen Sling for the Treatment of Female Stress Urinary Incontinence," J. Urol., http://home.satx.rr.com/sgsu/usurg/protegen.html (1997).
Eglin, G., et al., "Transobturator subvesical mesh. Tolerance and short-term results of a 103 case continuous series," Gynecology Obstetrique & Fertilite, Jan. 2003;31(1):14-19(6).
EP 03751825.5 Supplementary European Search Report dated Jun. 19, 2009.
EP 06789465.9 filed Aug. 3, 2006 Search Report dated Apr. 28, 2010.
EP 06800736.8 filed Aug. 3, 2006 Examination Report dated Feb. 24, 2012.
EP 06800736.8 filed Aug. 3, 2006 Search Report dated Apr. 26, 2010.
EP 06800736.8 Summons to attend oral proceedings dated Jan. 22, 2013.
EP 06824802.0 filed Aug. 3, 2006 Search Report dated Dec. 13, 2010.
EP 06846828.9 filed Dec. 28, 2006 Office Action dated May 18, 2010.
EP 06846828.9 filed Dec. 28, 2006 Official Minutes dated Oct. 12, 2012.
EP 06846828.9 filed Dec. 28, 2006 Search Report dated Apr. 26, 2010.
EP 07753112.7 filed Mar. 15, 2007 Supplemental European Search Report dated Dec. 30, 2010.
Falconer, C., Ekman-Ordeberg, G., Malmstrom, A., Ulmsten, U.; "Clinical Outcome and Changes in Connective Tissue Metabolism After Intravaginal Slingplasty in Stress Incontinent Women"; The International Urogynecology Journal; vol. 7, pp. 133-137, 1996.
Falconer, C., Soderberg, M., Blomgren, B., Ulmsten, U.; "Influence of Different Sling Materials on Connective Tissue Metabolism in Stress Urinary Incontinent Women"; The International Urogynecology Journal; S19-S23, 2001.
Ghoniem, Gamal et al., "Modified Pubovaginal Sling and Martius Graft for Report of the Recurrent Vesicovaginal Fistula Involving the Internal Urinary Sphincter," Eur Urol 1995; 27:241-245.
Glowacki, Ca, et al., "Bone anchors in urogynecology," Clin Obstet Gynecol, Sep. 2000;43(3):659-69, Review.
Gomelsky, Alex, et al., "Biocompatibility Assessment of Synthetic Sling Materials for Female Stress Urinary Incontinence," The Journal of Urology, Oct. 2007, vol. 178, pp. 1171-1181.
Gormley, E. Ann et al., "Pubovaginal slings for the management of urinary incontinence in female adolescents," The Journal of Urology, vol. 152, pp. 822-825, Aug. 1994.
Horbach, Nicolette S.; "Suburethral Sling Procedures"; Urogynecology and Urodynamics Theory and Practice Fourth Edition; Chapter 42, pp. 569-579, 1996.
Image, <http://www.ivstunneller.com/images/anterior-procedure.jpg>printed on Jul. 10, 2006.
Image, www.obgyn.neUurogyn/articles/moore_cystocele , printed Jul. 10, 2006 and Mar. 10, 2011, <http://www.obgyn.neUurogyn/articles/moore_cystocele>.
Iosif, S., et al., "Urodynamic studies of women with prolapse and stress incontinence before and after surgical repair," Urodynamics Studies, 101:1433-1442 (1979).
Jacquetin B., "Bladder suspension exclusively through the vagina: at last!" J Gynecol Obstet Biol Reprod 1991;20 (8):1143-4, Paris.
Jacquetin B., "Genital prolapses. Diagnosis," Rev Prat. Sep. 15, 2001;51(14):1609-16.
Jacquetin B., "Use of "TVT" in surgery for female urinary incontinence," J Gynecol Obstet Biol Reprod, May 2000;29(3):242-7.
Johnson & Johnson (Article), "Gynecare Prolift Systems: You Know Where You Want to Go . . . GPS for Pelvic Floor Repair," <http://www.jnjgateway.com/home.jhtml?loc=USENG&page=viewContent&contentId=09008b98>8102f39b&parentId=09008b988102f39b (2006).
Johnson & Johnson Gateway®, "Optimal technique for access to anatomic landmarks," <http://www.jnjgateway.com/home.html?loc=USENG&page=viewContent&contentID=090> (2005).
Johnson & Johnson Gateway®: Gynecare Prolift Innovative Design, http://www.jnjgateway.com/home.jhtml?loc=USENG&page=viewContent&contentID=090 (2005).
Johnson & Johnson Gateway®: Gynecare TVT Abdominal Approach, <http://www.jnjgateway.com/home.jhtml?loc=USENG&page=vieewContent&contentID=090> (2005).
Johnson & Johnson Gateway®: Gynecare TVT Obturator System, "Tension-Free Support for Incontinence" <http://www.jnjgateway.com/home.jhtml?loc=USENG&page=viewContent&contentID=090> (2005).
Johnson & Johnson Gateway®: Vaginal Approach, <http://www.jnjgateway.com/home.jhtml? loc=USENG&page=viewContent&contentID=090> (2005).
JP 2008-525210 filed Feb. 1, 2008 Office Action dated Oct. 5, 2011.
JP 2008-525211 filed Feb. 1, 2008 Office Action dated Oct. 31, 2011.
JP 2008-525252 filed Aug. 3, 2006 Office Action dated Aug. 26, 2011.
JP 2008-525252 filed Aug. 3, 2006 Office Action dated May 11, 2012.
JP 2008-548841 filed Jun. 27, 2008 Office Action dated Jan. 19, 2012.
JP 2008-548841 filed Jun. 27, 2008 Office Action dated Nov. 28, 2012.
Karlovsky, Matthew E., et al., "Surgical Treatment of Stress Urinary Incontinence", Journal of Urology, 2003.
Karmarkar, Santoshi J., et al., "The 3-loop technique: A reliable technique for anterior pubic fixation in bladder exstrophy," The Journal of Urology, Sep. 1995 vol. 154, 1173-1176.

(56) References Cited

OTHER PUBLICATIONS

Karram, Mickey M ., Bhatia, Narender N.; "Patch procedure: Modified Transvaginal Fascia Lata Sling for recurrent or severe stress urinary incontinence"; Obstetrics and Gynecology, pp. 461-463, Mar. 1990.
Kelly, Mark J. et al., "Symptom analysis of patients undergoing modified Pereyra bladder neck suspension for urinary stress incontinence," Urology, vol. 37, No. 3, Mar. 1991.
Kersey, J., "The guaze hammock sling operation in the treatment of stress incontinence," British Journal of Obstetrics and Gynaecology, vol. 90, pp. 945-949, Oct. 1983.
Kil, P.J.M. et al., "Transvaginal ultrasonography and urodynamic evaluation after suspension operations: comparison among the Gittes, Stamey and Burch suspensions," The Journal of Urology, vol. 146, pp. 132-136, Jul. 1991.
Kobashi, Kathleen C., et al., "Erosion of Woven Polyester Pubovaginal Sling," The Journal of Urology, Dec. 1999, vol. 162, pp. 2070-2072.
Korda, Andrew; Peat, Brian; Hunter, Peter; "Experience with Silastic Slings for Female Urinary Incontinence"; Aust NZ J Obstet Gynaecol, pp. 150-154, 1989.
Korman, Howard J. et al., "Success rate of modified Pereyra bladder neck suspension determined by outcomes analysis," The Journal of Urology, vol. 152, pp. 1453-1457, Nov. 1994.
Lichtenstein, Irving L., Shulman, Alex G., Amid, Parviz K., Montllor, Michele M.; "The Tension-Free Hernioplasty"; The American Journal of Surgery, vol. 157; Feb. 1989.
McIndoe, G.A.J., Jones, R.W., Grieve B.W.; "The Aldridge Sling Procedure in the Treatment of Urinary Stress Incontinence"; Aust NZ J Obstet Gynaecol; 1987.
MedlinePlus Medical Encyclopedia, "Female urinary tract," http://www.nlm.nih.gov/medlineplus/ency/imagepages/1122.htm (2004).
Miklos et al., Laparoscopic Urogynecology Center of Atlanta—Dr. Miklos & Dr. Moore, "Laparoscopic and Minimally Invasive Procedures, 'Tension Free Vaginal Tape (TVT) Sling'" printed Jul. 12, 2006; <http://www.urogynecologychannel.net/lap_proc12.php>.
Miklos et al., Vaginal prolapse relaxation and enterocele repair, printed Jul. 12, 2006; http://www.urogynecologychannel.net/prolapse6.php.
Miklos et al., Vaginal prolapse relaxation, posterior vaginal wall prolapse, printed Jul. 12, 2006; http://www.urogynecologychannel.net/prolapse3.php.
Miklos et al., Vaginal prolapse relaxation, uterine prolapse, printed Jul. 12, 2006; <http://www.urogynecologychannel.net/prolapse4.php>.
Miklos et al., Vaginal prolapse relaxation, uterosacral ligaments, printed Jul. 12, 2006; http://www.urogynecologychannel>.net/prolapse2a.php.
Miklos et al., Vaginal prolapse relaxation, vaginal vault prolapse, printed Jul. 12, 2006; <http://www.urogynecologychannel.net/prolapse5.php>.
Miklos et al., Vaginal relaxation, vaginal prolapse relaxaton, enterocele repair, Types of Vaginal Prolapse, printed on Jul. 12, 2006, http://www.urogyneocologychannel.net/prolapse.php?id=Prolapse.
Moore, Robert D., "Transobturator Approach for Cystocele Repair With Anterior Wall Mesh," <http://www.obgyn.net/hysterectomy-alternatives/hysterectomy-alternatives.asp>? page=urogyn/articles/moore_cystocele (2006).
Morgan, J.E.; "A sling operation, using Marlex polypropylene mesh, for treatment of recurrent strss incontinence." vol. 106, No. 3, pp. 369-377, Feb. 1970.
Mubiayi N., et al., "Surgical cure of stress urinary incontinence with vaginal tissue sling: technique, results, indications," Prog Urol. Feb. 2002;12(1):60-9.
Narik, G., Palmrich, A.H.; "A simplified sling operation suitable for routine use"; American Journal of Obstetrics & Gynecology, vol. 84, No. 3, Aug. 1962.
Netterimages.com, "Cystocele, Urethrocele," Image No. 5192, printed Jul. 24, 2006; <http://ww.netterimages.com/images/vpv/000/000/005/5192-05>. . . .
Netterimages.com, "Rectocele, Enterocele," Image No. 5193, printed Jul. 24, 2006; <http://www.netterimages.com/image/5193.htm>.
Nguyen, JK, "Current concepts in the diagnosis and surgical repair of anterior vaginal prolapse due to paravaginal defects," Obstet Gynecol Surv, Apr. 2001;56(4):239-46.
Nichols, David H.; "The Mersilene Mesh Gauze-Hammock for Severe Urinary Stress Incontinence"; Obstetrics and Gynecology; Obstetrics & Gynecology, vol. 41, No. 1, pp. 88-93, Jan. 1973.
Nickel, RF, et al, "Evaluation of a transpelvic sling procedure with and without colposuspension for treatment of female dogs with refractory urethral sphincter mechanism incompetence." Vet Surg. Mar.-Apr. 1998;27(2):94-104.
Norris, Jeffrey P., Breslin, David S., Staskin, David R.; "Use of Synthetic Material in Sling Surgery: A Minimally Invasive Approach"; Journal of Endourology; vol. 10, No. 3, Jun. 1996.
O'Donnell, Pat D.; "Combined Raz Urethral Suspension and McGuire Pubovaginal Sling for Treatment of Complicated Stress Urinary Incontinence"; Journal of the Arkansas Medical Society, vol. 88, No. 8, pp. 389-392, Jan. 1992.
Okoshi, Takafumi, et al., "Long-term Results of a New Antithrombogenic Cardiac Wall Substitute," Trans Am Soc. Artif Intern Organs, XXXV:391-395 (1989).
Parra, O. et al., "Experience with a Simplified Technique for the Treatment of Female Urinary Incontinence," The British Journal of Urology (1990), 66, 615-617.
PCT/AU2000/001298 filed Oct. 20, 2000 International Preliminary Examination Report dated Jan. 29, 2002.
PCT/AU2000/001298 filed Oct. 20, 2000 Search Report dated Jan. 3, 2001.
PCT/US03/24212 filed Aug. 1, 2003 International Search Report dated May 28, 2004.
PCT/US03/24212 filed Aug. 1, 2003 Written Opinion dated Aug. 24, 2004.
PCT/US07/78308 filed Sep. 12, 2007 International Search Report dated Jun. 5, 2008.
PCT/US07/78308 filed Sep. 12, 2007 Written Opinion dated Jun. 5, 2008.
PCT/US2003/013113 filed Apr. 28, 2003 International Preliminary Examination Report dated Oct. 14, 2004.
PCT/US2003/013113 filed Apr. 28, 2003 International Seach Report dated Oct. 15, 2003.
PCT/US2003/024212 filed Aug. 1, 2003 International Search Report dated May 24, 2004.
PCT/US2003/024212 filed Aug. 1, 2003 Written Opinion dated Aug. 24, 2004.
PCT/US2006/030369 filed Aug. 3, 2006 International Preliminary Report on Patentability dated Mar. 31, 2009.
PCT/US2006/030369 filed Aug. 3, 2006 Search Report dated Aug. 12, 2008.
PCT/US2006/030369 filed Aug. 3, 2006 Written Opinion dated Aug. 12, 2008.
PCT/US2006/030370 filed Aug. 3, 2006 International Preliminary Report on Patentability dated Feb. 4, 2008.
PCT/US2006/030370 filed Aug. 3, 2006 Search Report dated Jul. 20, 2007.
PCT/US2006/030370 filed Aug. 3, 2006 Written Opinion dated Jul. 20, 2007.
PCT/US2006/030581 filed Aug. 3, 2006 International Preliminary Report on Patentability dated Mar. 17, 2009.
PCT/US2006/030581 filed Aug. 3, 2006 Search Report dated Jul. 7, 2008.
PCT/US2006/030581 filed Aug. 3, 2006 Written Opinion dated Jul. 7, 2008.
PCT/US2006/062639 filed Dec. 28, 2006 International Preliminary Report on Patentability dated Oct. 7, 2008.
PCT/US2006/062639 filed Dec. 28, 2006 Search Report dated Oct. 1, 2007.
PCT/US2006/062639 filed Dec. 28, 2006 Written Opinion dated Oct. 1, 2007.
PCT/US2007/006461 filed on Mar. 15, 2007 International Preliminary Report on Patentability dated Sep. 16, 2008.

(56) References Cited

OTHER PUBLICATIONS

PCT/US2007/006461 filed on Mar. 15, 2007 Search Report dated May 22, 2008.
PCT/US2007/006461 filed on Mar. 15, 2007 Written Opinion dated May 22, 2008.
PCT/US2008/083381 filed Nov. 13, 2008 International Search Report dated Dec. 29, 2008.
PCT/US2008/083381 filed Nov. 13, 2008 Written Opinion of the International Searching Authority dated Dec. 29, 2008.
Pelosi, Ma, et al., "The transobturator sling: newest tension-free suburethral sling for treatment of stress urinary incontinence," Surg Technol Int. 2004;13:173-9. Review.
Petros, Peter E. Papa et al., "The Combined Intravaginal Sling and Tuck Operation. An Ambulatory Procedure for Cure of Stress and Urge Incontinence," Acta Obstet Gynecol Scan Suppl 153: 53, pp. 115-117, 1990.
Petros, Peter E. Papa, "Ambulatory surgery for urinary incontinence and vaginal prolapse," Med. J. of Australia, 161:171-172 (1994).
Raz, Shlomo et al., "The Raz Bladder Neck Suspension: Results in 206 Patients," The Journal of Urology, vol. 148, pp. 845-850, Sep. 1992.
Raz, Shlomo; Female Urology; Second Edition; Selected Chapters, © 1996.
Ridley, John H.; "Appraisal of the Goebell-Frangenheim-Stoeckel sling procedure"; American Journal of Obstetrics & Gynecology, vol. 95, No. 5, pp. 714-721, Jul. 1966.
EP 06827826.6 filed May 14, 2008 Supplementary Search Report dated Feb. 4, 2011.
PCT/US2006/044315 filed Nov. 14, 2006 International Preliminary Report on Patentability dated Mar. 24, 2009.
PCT/US2006/044315 filed Nov. 14, 2006 International Seach Report dated May 6, 2008.
PCT/US2006/044315 filed Nov. 14, 2006 Written Opinion dated May 6, 2008.
U.S. Appl. No. 12/093,493, filed Jul. 14, 2008 Final Office Action dated Jul. 6, 2011.
U.S. Appl. No. 12/093,493, filed Jul. 14, 2008 Non-Final Office Action dated Jan. 20, 2011.
U.S. Appl. No. 12/093,493, filed Jul. 14, 2008 Notice of Allowability dated Sep. 22, 2011.
AU 2008320999 Patent Examination Report No. 1 dated May 10, 2013.
AU 2013203711 filed Apr. 11, 2013 Examination Report No. 1 dated May 10, 2013.
EP 08849041.2 extended European Search Report dated Mar. 12, 2013.
MX/a/2010/005271 Office Action dated Mar. 7, 2013.
U.S. Appl. No. 13/524,408, filed Jun. 15, 2012 Notice of Allowance dated Jun. 24, 2013.
EP 06827826.6 filed May 14, 2008 Intent to Grant dated Oct. 30, 2013.
EP 08849041.2 Official Action dated Nov. 12, 2013.
U.S. Appl. No. 14/070,102, filed Nov. 1, 2013 Final Office Action dated Apr. 8, 2014.
U.S. Appl. No. 14/070,102, filed Nov. 1, 2013 Non-Final Office Action dated Dec. 24, 2013.

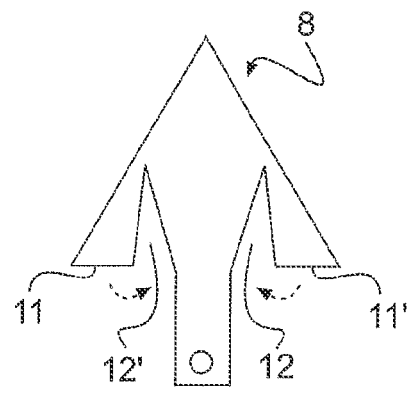
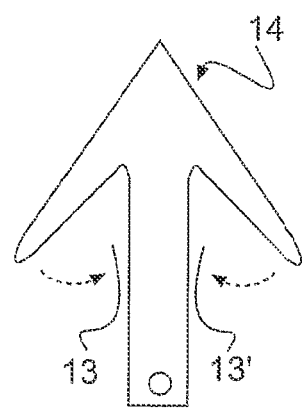
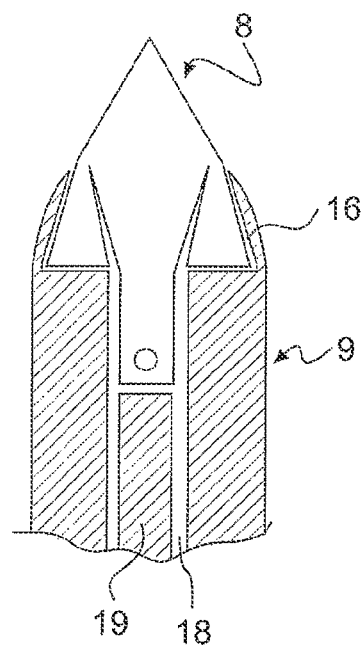
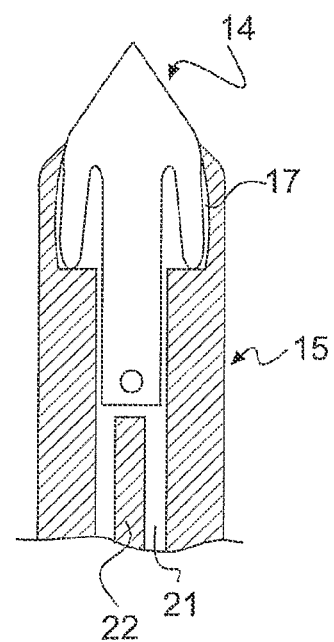
FIG. 1E          FIG. 1F

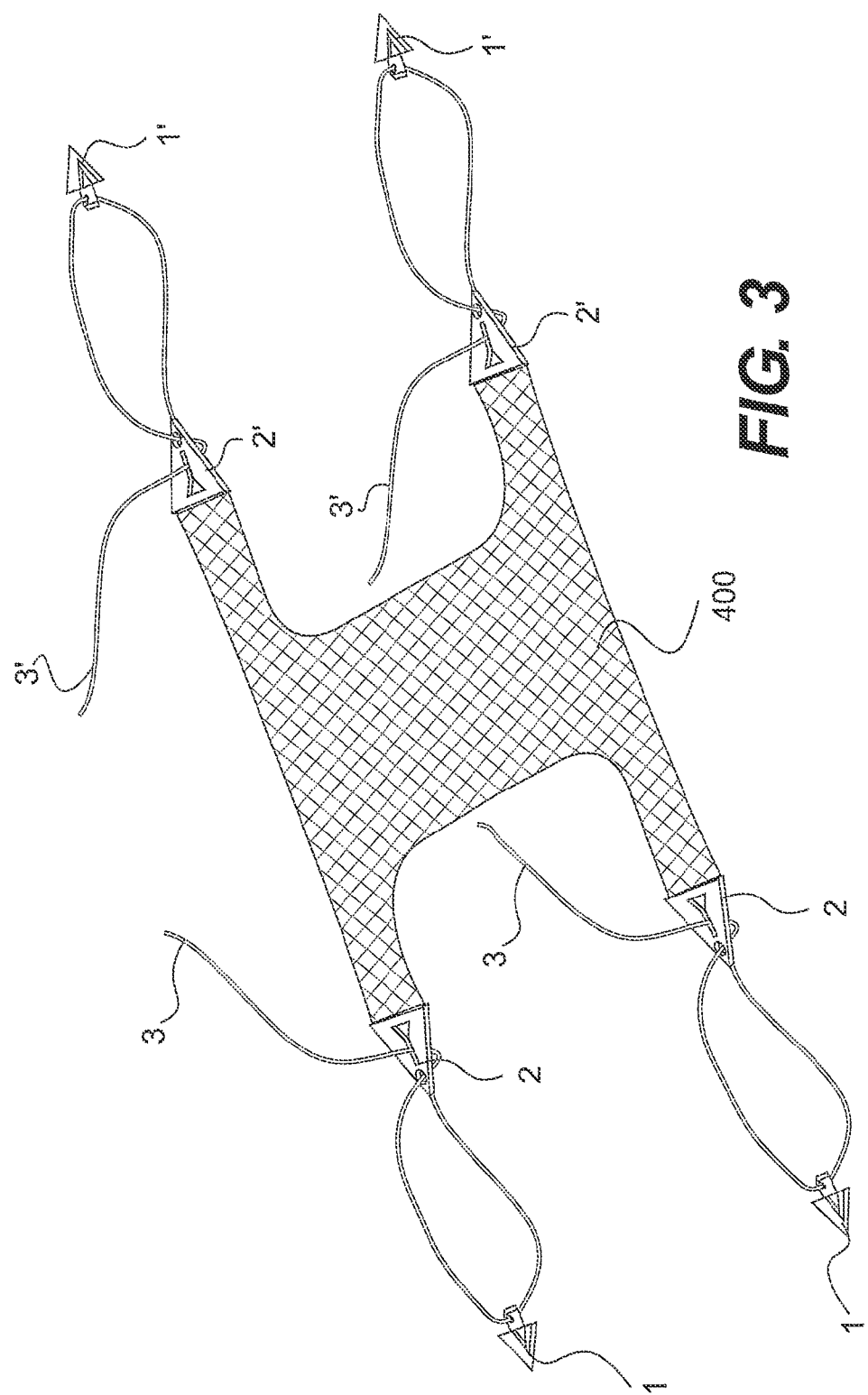

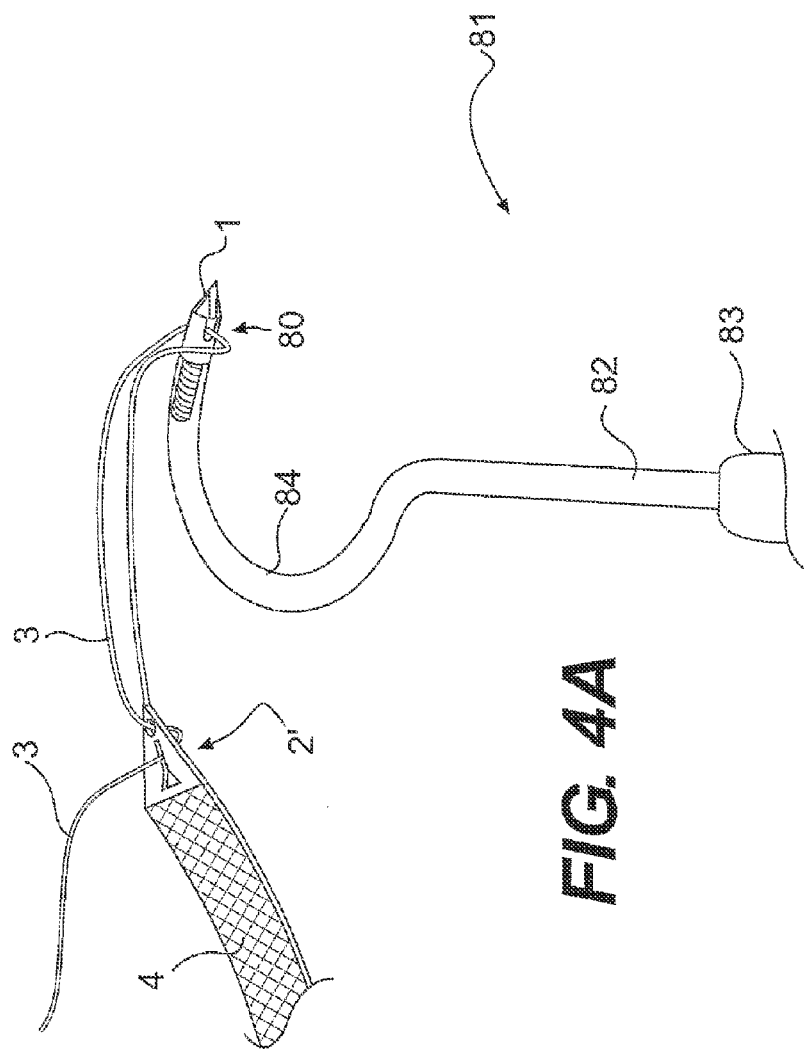

SLING ANCHOR SYSTEM

This application is a continuation of U.S. patent application Ser. No. 12/093,493, now U.S. Pat. No. 8,092,366, filed as a U.S. national stage application under 35 U.S.C. §371 of International Application No. PCT/US2006/044315, filed Nov. 14, 2006, claiming priority to U.S. Provisional Patent Application No. 60/736,219, filed Nov. 14, 2005, to U.S. Provisional Patent Application No. 60/749,774, filed Dec. 13, 2005, and to U.S. Provisional Patent Application No. 60/754,540, filed Dec. 28, 2005, the disclosures of which are all incorporated herein by reference in their entirety.

The present invention relates generally to the treatment of stress urinary incontinence using at least one of an improved anchor, introducer system, and tensioning system.

An increasingly widespread technique for treating urinary incontinence is that of sling suspension. Examples of such procedures and equipment that can be employed are discussed in U.S. Pat. Nos. 5,112,344, 5,899,909, and 6,273,852; and U.S. Patent Application Publication Nos. U.S. 2004/0144395, and U.S. 2006/0015069, the disclosures of which are all incorporated by reference herein in their entirety.

Generally, sling suspension procedures involve the placement of a sling member beneath the patient's urethra. The sling member is suitably implanted in the patient's tissue by using an introducer needle to help draw the tissue implant sling into position.

Slings have been made from tape or mesh. Numerous implant materials have been considered and used for sling procedures, including both synthetic and natural materials.

A traditional sling procedure involves placing a strip of an implant material (natural tissue or synthetic mesh) under the urethra and securing it to the rectus fascia or other portions of the patient's anatomy with sutures to hold the implant in position during the healing process.

Techniques have been developed that speed the implant process, by reducing the number of incisions made and altering the pathways by which the tissue implant is introduced into the body. These improvements, which employ specialized instrumentation, help to reduce operative time and have made the procedure less invasive.

These techniques generally require that an implant be joined to an introducer needle. Typically, the implant is inserted into, and pulled through the body. Then, in a subsequent step, the implant is detached from the introducer needle. A deficiency with existing introducer devices, however, is that they are typically unwieldy, awkward, and it can be time consuming to attach and/or detach an implant to or from an introducer device.

Accordingly, it could be advantageous to provide a system for implanting an article that avoids at least one of the foregoing deficiencies.

According to various embodiments, the present disclosure is directed to an implantable system comprising at least two tissue anchors, at least two filamentary elements adapted to be associated with the at least two tissue anchors, and a support member comprising at least two connectors, wherein the at least two connectors are adapted to associate the support member with the at least two filamentary elements, and wherein at least one of the at least two connectors is adapted to adjustably and releasably fix a filamentary element.

According to various embodiments, the present disclosure is directed to a method for providing support for a female urethra, comprising creating an incision in the anterior vaginal wall just below the urethral meatus, advancing an introducer needle through the incision and towards the direction of one of the two obturator foramen where the introducer needle has a tissue anchor connected to its distal end, and releasing the anchor from the introducer needle, wherein the anchor is connected to a support member via a filamentary element.

According to various embodiments, there is provided a kit for providing support to a female urethra, comprising at least one introducer needle, at least two soft tissue anchors adapted to be connected to the at least one introducer needle, and at least one implantable article comprising a support portion, wherein the implantable article comprises at least two connectors, each of which has at least one filamentary element attached thereto, and wherein the at least two connectors each contain at least one perforation for adjustably and releasably fixing a filamentary element.

BRIEF DESCRIPTION OF THE DRAWINGS

The present invention is further described in the detailed description which follows, in reference to the noted drawings, by way of non-limiting examples of certain embodiments of the present invention, in which like characters represent like elements throughout the views of the drawings, and wherein:

FIG. 1E illustrates a configuration of an anchor seated in the distal end of an introducer needle in accordance with various aspects of the present disclosure.

FIG. 1F illustrates a configuration of an anchor seated in the distal end of an introducer needle, in accordance with various aspects of the present disclosure.

FIG. 3 illustrates an implantable system configured for prolapse repair, in accordance with various aspects of the present disclosure.

FIG. 4A illustrates an example of a curved introducer needle associated with an implantable system in accordance with various aspects of the present disclosure.

The present disclosure is directed generally to various systems, methods, and articles of manufacture suitable for treating various disorders including, by way of example, at least one of urinary incontinence, rectocele, cystocele, and enterocele. However, the systems, methods, and article of manufacture disclosed herein can also have other uses. For example, they may be used to provide adjustable tension between two points, such as ligaments, tendons, etc., within the body. The systems disclosed herein provide advantages over prior art systems. For example, the anchors disclosed herein can be used as the tissue dissectors. Also, according to various embodiments, the anchors can provide both one- and two-way adjustability.

Figure 1A:
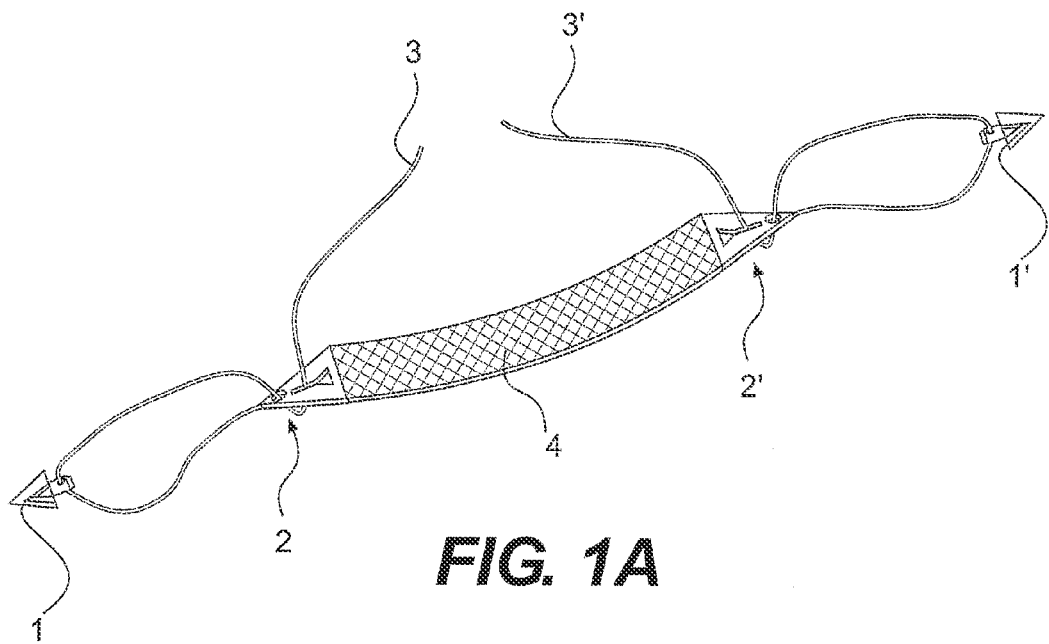
FIG. 1A illustrates one embodiment of an implantable system in accordance with the present invention.

FIG. 1A illustrates one embodiment of an implantable system according to various embodiments. Tissue anchors 1 and 1' are adapted to be inserted and anchored into body tissue, such as ligament, muscle, fascia, and other tissues capable of holding an anchor. Support member 4 is configured to provide support to tissue within the body, such as a urethra, bladder neck, bladder, rectum, etc. The support member 4 comprises connectors 2 and 2'. The connectors 2 and 2' are, according to various embodiments, attached to support member 4. The connectors may be a separate article from the support member, and is joined during the manufacturing process by methods well-known to the ordinary practitioner, such as heat bonding, adhesive application, etc. According to another embodiment, the connectors are integral with the support member 4. According to another embodiment, the connectors are designed to be joined to support member 4 in a securable fashion by a physician.

Figure 1B:
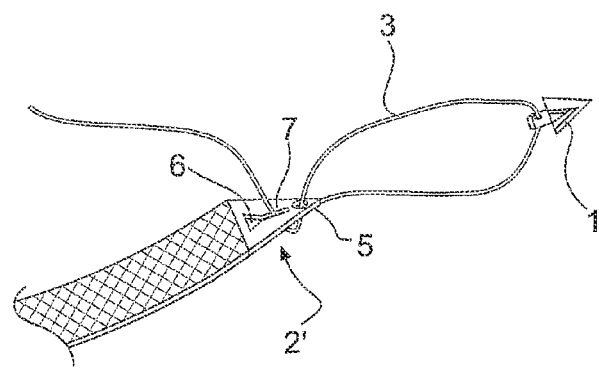
FIG. 1B is an expanded view of one embodiment of the implantable system according to FIG. 1A.

With reference to FIGS. 1A and 1B, filamentary elements 3 and 3' associate the support member with the anchors 1 and 1', respectively. According to various embodiments, and with reference to the right side of the implantable system, one end of the filamentary element 3' is permanently attached to connector 2', which in turn is connected to support member 4. The other end of filamentary element 3' is first threaded through tissue anchor 1', and is then threaded through a first aperture 5 in connector 2', and then through a second aperture 6 in the connector. According to various embodiments, second aperture 6 contains a cleating member 7, so that the free end of the filamentary element 3 can be releasably fixed in connector 2'. According to various embodiments, filamentary element 3' and aperture 5 in connector 2' allows the physician to adjust the tension of the support member 4 when, e.g., it is looped beneath a urethra.

By way of illustration, and with reference to FIG. 1A, anchor 1 may be secured in the obturator internus muscle, the support member may be disposed underneath the urethra, and then anchor 2' may be disposed in the contralateral obturator internus muscle. It can then be desirable to adjust the tension exerted by the support member on the urethra by pulling on at least one of the two filamentary elements 3 and 3'. When the desired amount of tension is obtained, the physician may then secure one or both filamentary elements by passing them through both apertures in the connector and laterally into the cleating member.

Figure 1C:
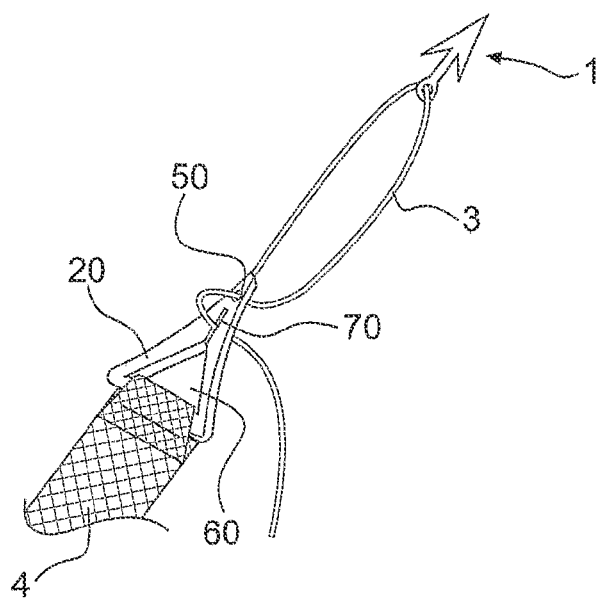
FIG. 1C illustrates an expanded view of one component of an implantable system in accordance with the present disclosure.

FIG. 1C illustrates another embodiment of a portion of an implantable system according to various embodiments. One end of filamentary element 3 is permanently secured in connector 20, and a free end of the filamentary element is drawn through an aperture in tissue anchor 1, through aperture 50, through aperture 60, and then secured in cleating member 70. Aperture 60 differs from aperture 6 in FIGS. 1A-1B in that aperture 60 is larger. The connector 20 comprises less material, which serves to minimize tissue trauma and abrasion, thereby reducing the risk of erosion to surrounding tissue. According to various embodiments, the edge comprising the internal circumference of aperture 60 can be blunted and rounded, such that no sharp edges are presented that might damage surrounding tissue.

Figure 1D:
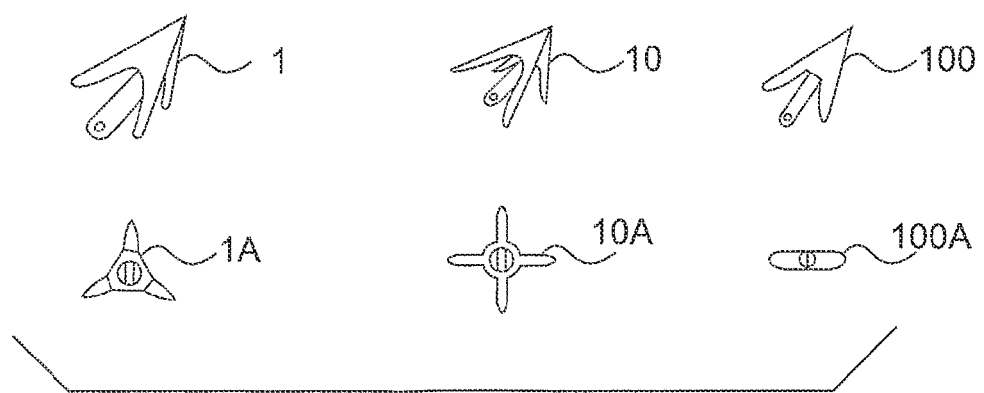
FIG. 1D illustrates various anchors from side and bottom perspectives, in accordance with the present disclosure.

According to various embodiments, FIG. 1D illustrates exemplary anchors useful in accordance with the present disclosure. Anchor 1 is a three barbed anchor, having a view 1A from the bottom of the anchor; anchor 10 is a four-barbed anchor, having a view from the bottom 10A; and anchor 100 is a two barbed anchor, with a view from the bottom 100A. Those of ordinary skill in the art will appreciate that various types of anchors may be used in accordance with the present disclosure, depending on the anchoring properties sought.

FIG. 1E illustrates the configuration of a tissue anchor 8 in the distal end of an introducer needle 9. The tissue anchor 8 has barbs 11 and 11' that extend laterally from its longitudinal axis. The barbs 11 and 11' are flexible in a direction substantially perpendicular to the longitudinal axis of the anchor, such that they can be urged toward or away from the longitudinal axis. This flexibility allows the anchor 8 to be securely seated in the distal end of the introducer needle 9 until the anchor is purposefully discharged into tissue by the physician.

As illustrated in FIG. 1E, the cavities 12 and 12' formed by the space between the anchor body and the barbs angles slightly away from the anchor body as the cavities extends towards the distal end of the anchor 8. This angle, combined with the wider proximal ends of the barbs, permits the anchor to be seated in the introducer needle with minimal flexing.

FIG. 1F illustrates another exemplary configuration of an anchor 14. There, the cavities 13 and 13' formed between the anchor body and the barbs extends distally in a direction parallel to the longitudinal axis of the anchor body. The proximal ends of the anchor barbs are also narrow relative to the proximal ends of the anchor barbs of anchor 8. This configuration may be desirable when anchors with a wider profile are desirable, such as for greater anchoring ability in a softer tissue.

The distal end of the introducer needles 9 and 15 have cavities 16 and 17, respectively, dimensioned to receive and securely house at least a portion of the anchors. An internal lumen 18 of introducer needle 9 comprises a stylet member 19, which is actuated in a distal direction by a control mechanism, such as a button-actuated spring (not shown). Similarly, internal lumen 21 of introducer needle 15 comprises a stylet member 22. Suitable actuating mechanisms are well-known in the art, and the selection of one over the other is a matter well-within the skill of the ordinary practitioner.

Figure 1G:
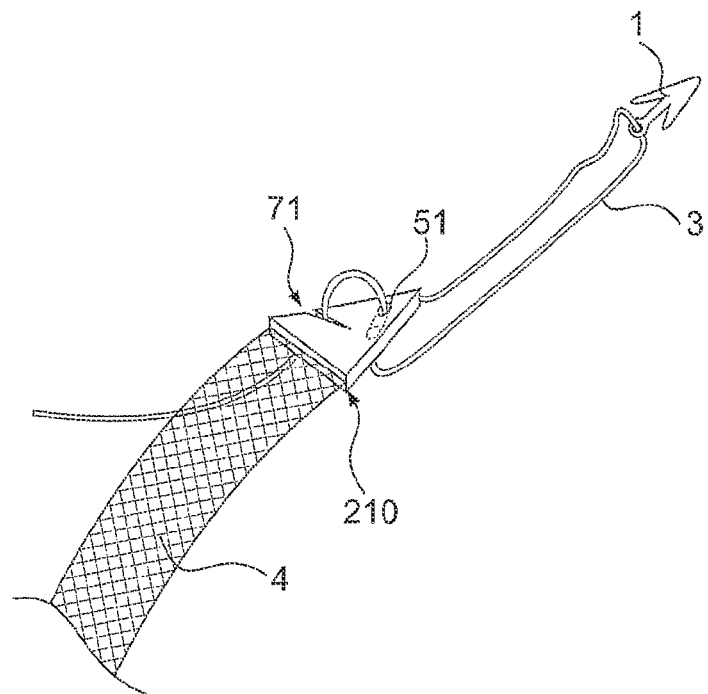
FIG. 1G illustrates an aspect of an implantable system in accordance with various aspects of the present disclosure.

According to various embodiments, FIG. 1G illustrates another suitable implantable system in accordance with the present disclosure. This implantable system comprises an anchor 210 with an aperture 51 and a cleating member 71. Cleating member 71 extends radially from the center, or near the center, of the connector and towards a lateral edge of the connector, much like a cleating member in a spool of thread. Filamentary element 3 extends from a permanent connection at the tip of connector 210, through an aperture in anchor 1, through aperture 51, and then into cleating member 71.

Figure 1H:
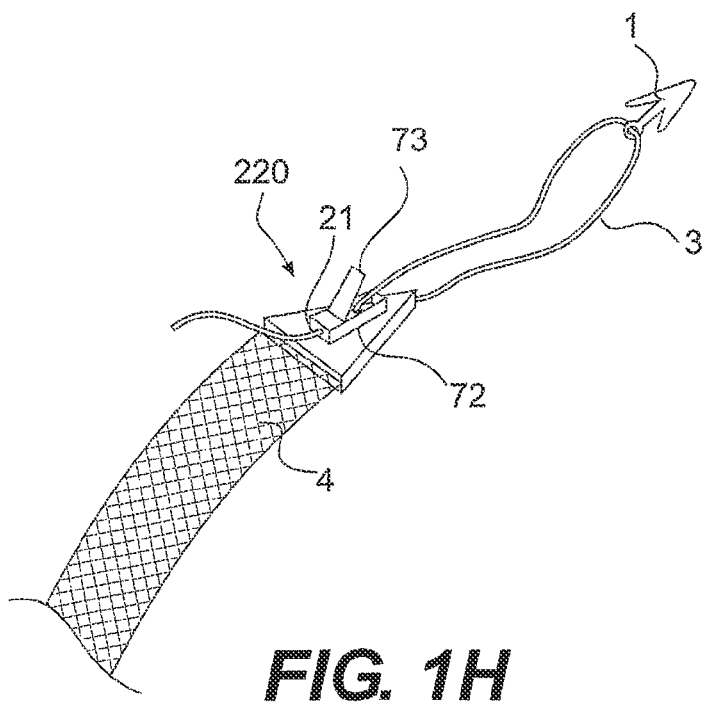
FIG. 1H illustrates an aspect of an implantable system in accordance with various aspects of the present disclosure.

FIG. 1H illustrates another connector in accordance with various embodiments. Connector 220 comprises a locking housing 72, with an internal lumen and a locking member 73. The filamentary element 3 is permanently connected at one end to connector 220, drawn though an aperture in anchor 1, and then though the locking housing 72. When the desired amount of filamentary element is drawn through locking housing 72, the locking member 73 is depressed into engagement with the housing to secure the filamentary element.

Figure 1I:
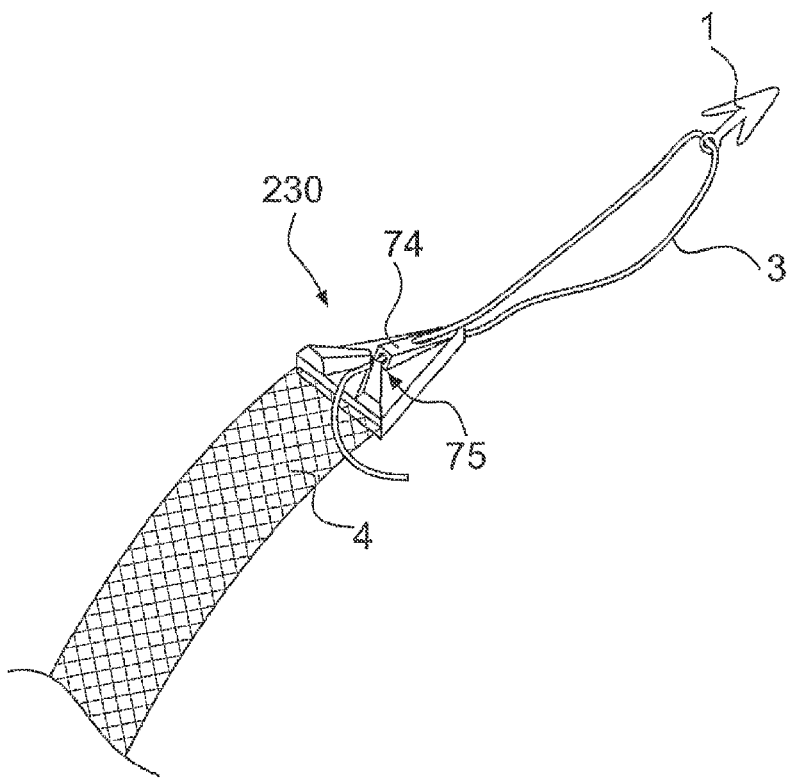
FIG. 1I illustrates an aspect of an implantable system in accordance with various aspects of the present disclosure.

Another exemplary connector 230 is illustrated in FIG. 1I. There, an external cleating element 75 is disposed proximate to lumened member 74. The filamentary element extends from a permanent connection at connector 230, through an aperture in anchor 1, and through lumened member 74 and towards external cleating element 75, wherein it may be fixed as shown.

Figure 2:
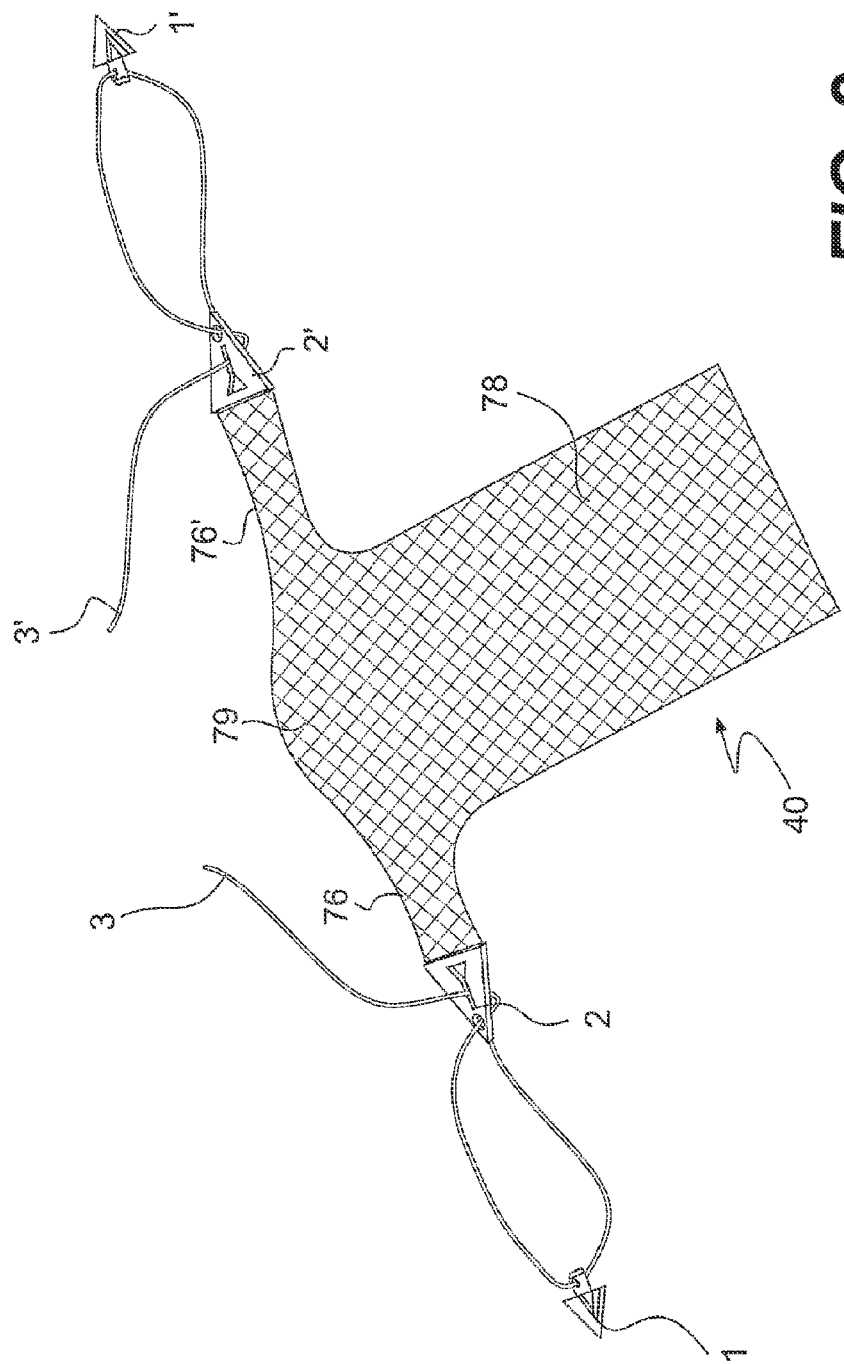
FIG. 2 illustrates an implantable system having a large central support body in accordance with various aspects of the present disclosure.

FIG. 2 illustrates one embodiment of an implantable system having a broad central support area in support member 40. Support member 40 is characterized by two lateral ends 76 and 76' terminating in connectors 2 and 2'; a central support body 78 extending in one direction; and a support portion 79 extending in the opposite direction.

According to various embodiments, FIG. 3 illustrates another embodiment of an implantable system. This embodiment comprises a support member 400 configured for vaginal prolapse repair, and is characterized by four arms, each of which terminates in respective connectors. The support member may be configured to treat various pelvic floor disorders such as, for example, a cystocele, which is a condition whereby the bladder descends into the vaginal vault.

The support member can be made of any suitable biocompatible material. For example, the support member can be made of a permanent material, partially bioabsorbable material, completely bioabsorbable material, or any combinations thereof. In some embodiments, the synthetic material comprises knitted monofilament, polypropylene mesh having multidirectional elasticity that provides long-term reinforcement of pelvic support structures. Irrespective of the material used to construct the implants, according to various embodiments the implants are highly flexible yet have the strength needed for tissue support.

The material can be a synthetic mesh, such as polypropylene mesh or bioabsorbable PLA. The support member can comprise a biological material, such as porcine dermal tissue, cadaveric tissue, collagen-based mesh, or other biological material suitable for implantation into an animal (e.g., human) body. The support member can comprise an identification element, such as one or more colored threads, or differently-shaped arms, to enable the physician to identify and track various aspects of the support member during placement.

According to various embodiments, suitable non-limiting examples of materials that can serve as support members include acellular porcine dermal tissue. Such dermal material is typically processed to render it biocompatible. One scheme for preparing biocompatible porcine dermal tissue is set forth in U.S. Pat. No. 5,397,353 to Oliver et al, and owned by Tissue Science Laboratories PLC, of Aldershot, Hampshire, U.K. Such material is commercially available as Pelvicol™ implant material, distributed by C. R. Bard, Inc. of Murray Hill, N.J., and produced by Tissue Science Laboratories PLC. Another suitable material is CollaMend™ implant, which is a sterile, off-white sheet of lyophilized acellular porcine dermal collagen that retains its constituent elastin fibers. CollaMend™ implant is also available from C. R. Bard, Inc.

The support member can have any dimensions suitable for its intended purpose. The support member can be narrow or wide, depending on the organ and/or tissue to be supported. For example, when used to support the urethra, the support member can have a width ranging from about 5 mm to about 20 mm, for example about 8 to about 12 mm. The length can range from about 2 to about 15 cm, for example from about 3 to about 10 cm.

The tissue anchor can be made of any suitable biocompatible material. By way of non-limiting example, suitable tissue anchors in accordance with the present disclosure can be constructed of silicone, stainless steel, Dacron, polypropylene, and any combination of the foregoing. The tissue anchors can be permanent, partially bioabsorbable, or completely bioabsorbable. Suitable non-limiting examples of bioabsorbable material include PLA copolymers, such as poly (L/D lactide) acid having a high inherent viscosity.

According to various embodiments, the tissue anchor provides fixation of the implantable systems disclosed herein. The anchors are designed to anchor into soft tissue such as muscle, fascia, and ligaments. The anchors have barbs that lock into the surrounding tissue when pressed into position. The barbs may be compressed initially during insertion, then expanded outwards when lodged into surrounding tissue, or they may be in an expanded position before, during, and after placement. According to various embodiments, the anchors are configured to hold a portion of a filamentary element. This configuration can comprise an aperture, or eyelet, disposed at the proximal end of the anchor that permits passage (and, optionally, fixation of) the filamentary element.

The anchor can optionally include a locking mechanism. For example, the locking mechanism can permit preferential, or one-way, movement of the filamentary element. This may be accomplished by a variety of means, such as by providing an eyelet bordered by a series of angle barbs. Suitable non-limiting examples of such anchors may be found in U.S. Patent Application Publication No. U.S. 2005/0256530, the disclosure of which is incorporated herein by reference in its entirety.

The filamentary element is designed to associate the support member with a tissue anchor. According to various embodiments, the filamentary element can be comprised of a variety of materials. It can comprise a permanent or bioabsorbable material. The filamentary element can comprise the same materials as, and optionally be integral with, the support member. According to various embodiments, the filamentary element can be a single- or multi-strand filament, such as single- or multi-strand polypropylene.

According to various aspects of the present disclosure, the implantable support system disclosed herein comprises at least one introducer needle. The introducer system disclosed herein provides a simple and efficient way to implant a support member, such as a urethral sling or a prolapse repair implant. The introducer needle may comprise a hook-shaped introducer needle that can be used for placing both arms of an implant, or it can comprise a helical or halo-shaped needle.

According to various embodiments, a kit comprising a helical or halo-shaped needle would comprise two needles, a left version and a right version, for placing each end of the implantable system in a patient.

The introducer needles disclosed herein can be made of any suitable biocompatible material such as stainless steel, nitinol, etc. If desired, the introducer needle could be coated with a low-friction layer of material (not shown) such as PTFE to reduce insertion trauma. According to various embodiments, the introducer needle and/or the support member can comprise an external sleeve. Such a sleeve could serve two purposes. First, if made of PTFE or similar material, it could provide a lubricious surface to ease passage of the introducer needle and/or the support member through the body, while at the same time minimizing injury to tissue. Secondly, the sleeve could be made of a bright color, such as green or blue, to improve visibility during an optional cytoscopy to confirm bladder integrity. Even if bladder perforation is not observed, the bright color of the sleeve can be seen through the thin bladder wall, confirming same placement of the introducer needle.

Figure 4B:
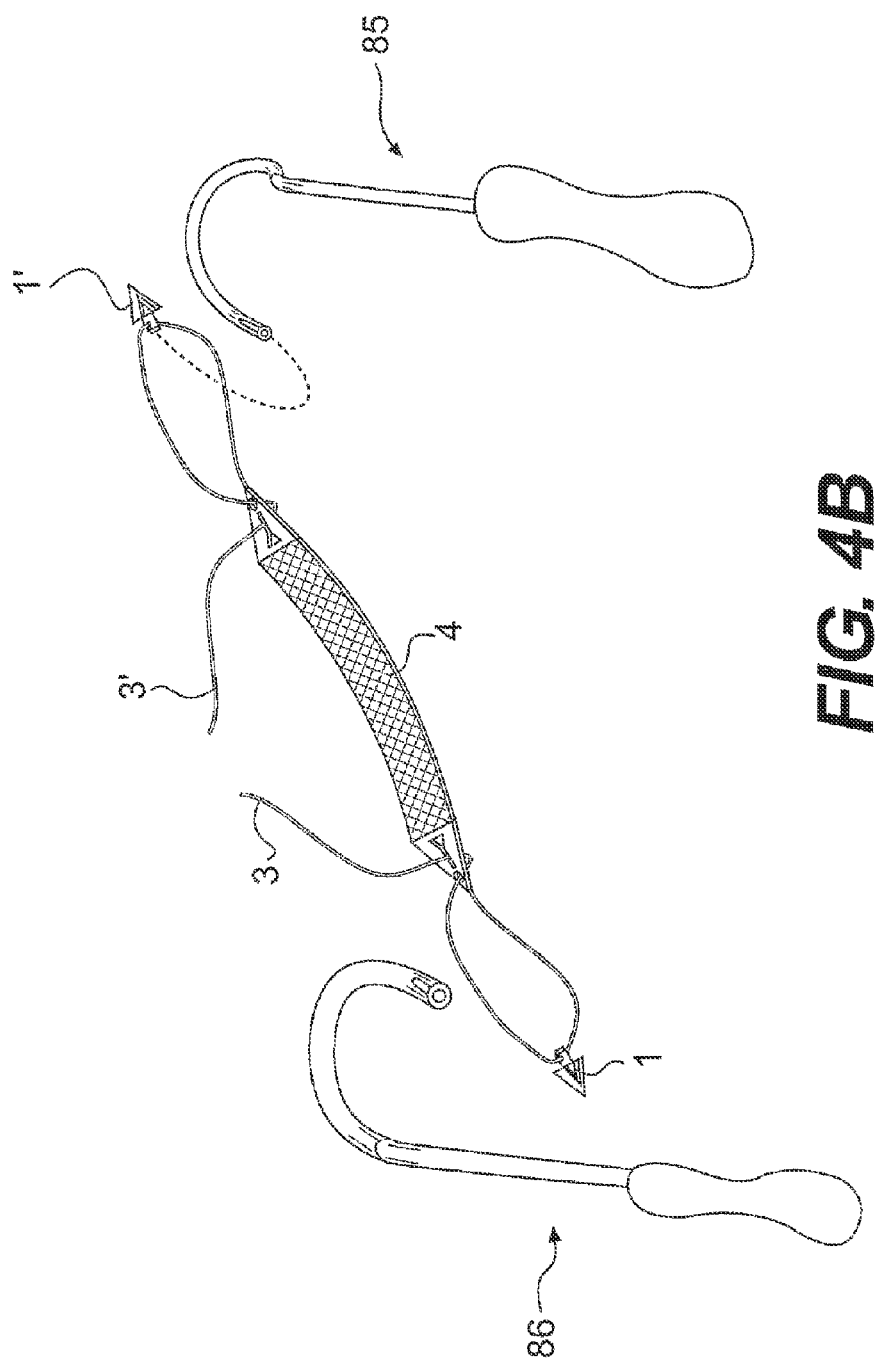
FIG. 4B illustrates various components of a kit for supporting the urethra, in accordance with various aspects of the present disclosure.
Figure 4C:
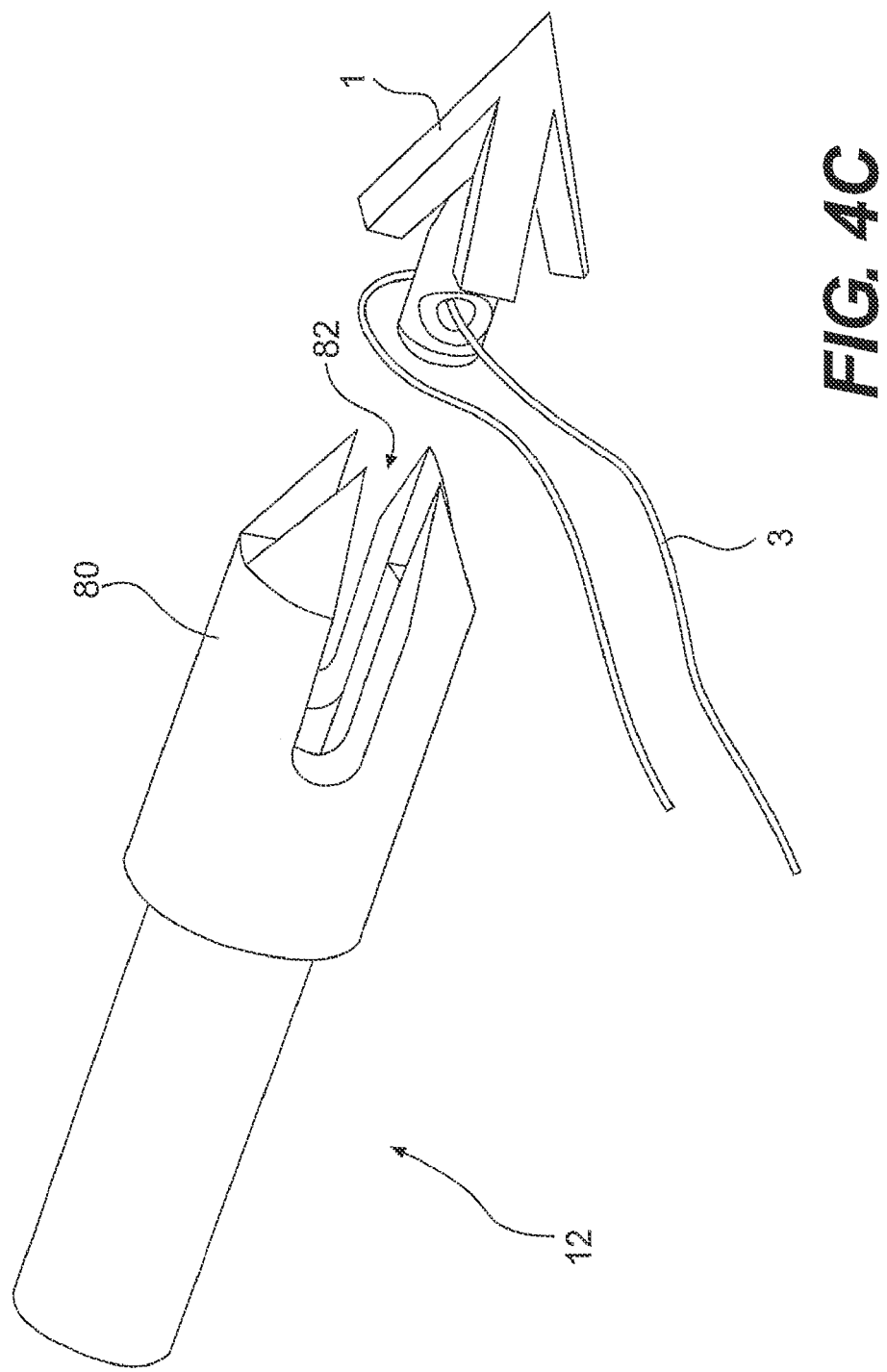
FIG. 4C illustrates an expanded view of an anchor and the distal end of an introducer needle, in accordance with various aspects of the present disclosure.

FIGS. 4A-4C illustrates an embodiment whereby tissue anchor 1 is mounted on the distal end 80 of introducer needle 81. Referring to FIG. 4A, introducer needle 81 comprises a shaft having a straight proximal portion 82 terminating in handle 83, and curved distal portion 84. The filamentary element 3 is looped through anchor 1, and the entire assembly is ready for use. According to various embodiments, FIG. 4B illustrates various aspects of a kit for treating urinary incontinence, including two halo needles 85 and 86, support member 4, filamentary elements 3 and 3', and tissue anchors 1 and 1'. FIG. 4C illustrates a detailed view of the distal end 80 of introducer needle 81 comprising a recess 82, into which a tissue anchor may be seated.

Figure 5A:
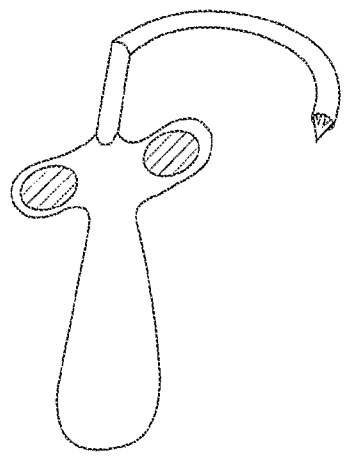
FIGS. 5A-F illustrate various introducer needles in accordance with various aspects of the present disclosure.
Figure 5B:
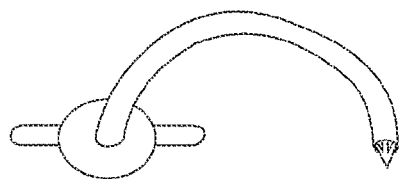
Figure 5C:
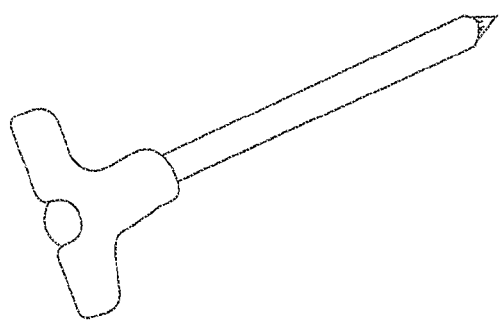

FIGS. 5A-5F illustrate various embodiments of an introducer needle. FIGS. 5A-5B illustrate a side view and top view, respectively, of a halo-shaped introducer shaft typically used for anchoring a support member in the region of the obturator foramina. FIG. 5C illustrates, in accordance with various aspects of the present disclosure, an introducer needle having a straight shaft.

According to various embodiments, the introducer needle can have a small dimensions relative to the introducer needles disclosed in the prior art. For example, the introducer needle can have small curve so that the tissue anchors cannot be inserted too deeply. This can allow for added patient safety during the procedure. The introducer needle can also be designed to have a small handle that can be held in the physician's fingertips or hand to minimize the bulkiness of the introducer and provide optimal tactile control.

Figure 5D:
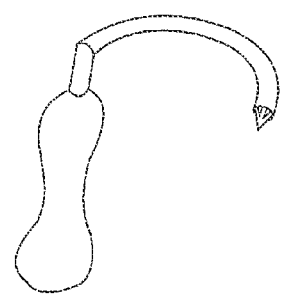
Figure 5E:
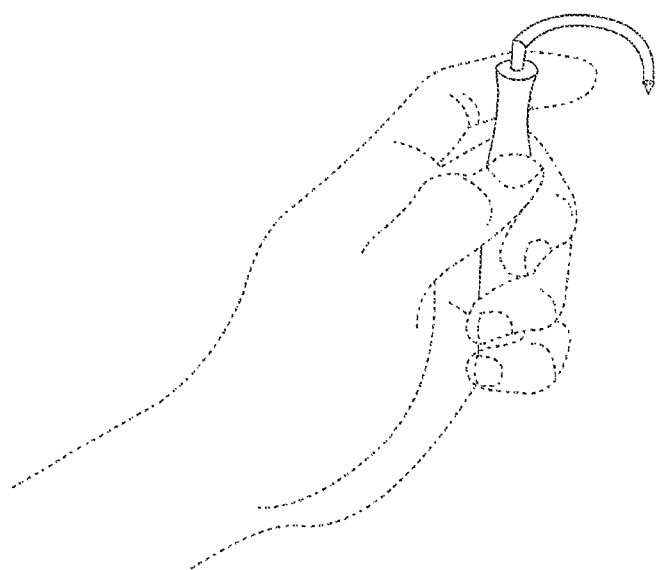
Figure 5F:
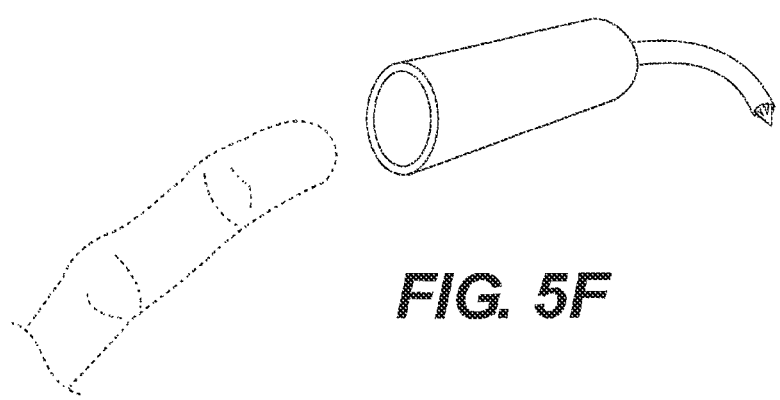

FIGS. 5D-5E illustrate halo introducer needles that are small relative to the needles disclosed in, e.g., U.S. 2006/0015069 (the disclosure of which is incorporated herein by reference in its entirety). In accordance with various embodiments, FIG. 5D illustrates a minimal pivot introducer needle, such that the needle is held by the fingertips as opposed to the entire hand. As shown in FIG. 5E, and in accordance with various embodiments, the index finger can wrap around the back of the needle shaft to urge the distal end (and hence the anchor) into the obturator internus muscle.

Figure 6A:
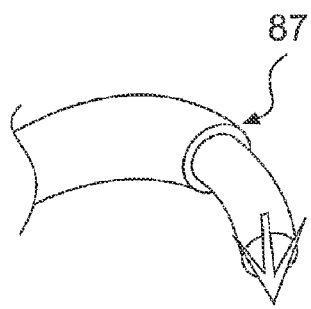
FIGS. 6A-B illustrates an introducer needle in accordance with various aspects of the present disclosure.
Figure 6B:
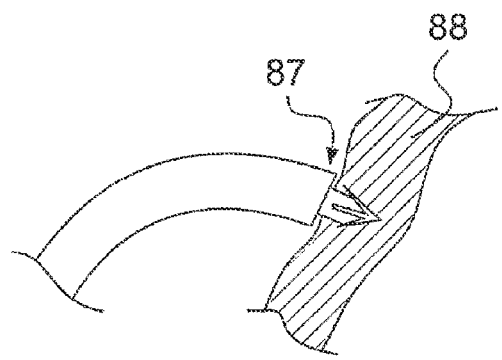

According to various embodiments, it could be desirable to provide an introducer needle with a "stop," or limiting element, that facilitates a limited insertion into the obturator internus muscle. For example, it may be advantageous to insert the tissue anchors into the obturator internus muscle without penetrating the obturator membrane. The needle illustrated in FIGS. 6A and 6B provide an element 87 that permits tactile feel when the distal end of the introducer needle is seated in the internus muscle 88, thereby signaling to the physician that the desired location is reached and further needle progression should stop.

The introducer needle in accordance with various aspects of the present disclosure comprises a distal end with a deployment head that holds the tissue anchor during positioning. When the tissue anchor is positioned in a desired location, the introducer can release the anchor either passively by retracting the introducer, or actively with a push-button, slide, or similar mechanism. The deployment head may also provide a means for compressing the barbs of the anchor so that there is less resistance when inserting the anchor into the tissue. After the anchor is deployed, the barbs can spring outward to lock into the surrounding tissue.

Figure 7:
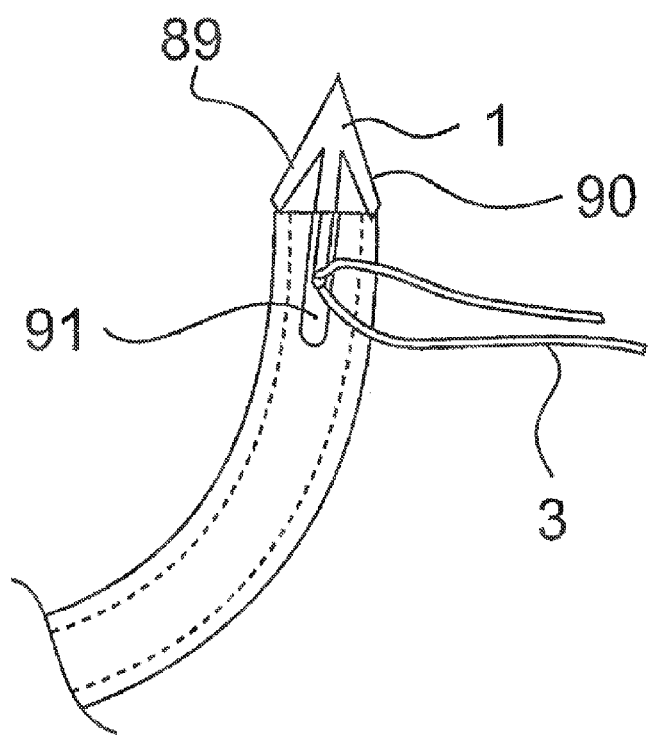
FIG. 7 illustrates one embodiment of an anchor seated in an introducer needle in accordance with various aspects of the present disclosure

Alternatively, and according to various embodiments, the deployment head can shield the barbs on the anchor to prevent the barbs from anchoring into the surrounding tissue until after deployment. As illustrated in FIG. 7, anchor 1 is seated at the distal end of introducer needle 81. The anchor barbs 89 and 90 are substantially flush with the circumference of the needle shaft. According to this aspect of the disclosure, the anchor barbs do not grasp in tissue until the anchor is deployed. The distal end of needle 81 comprises at least one slot 91, through which the filamentary element 3 may extend. According to various embodiments, in order to minimize tissue trauma during needle introduction, the distal end of the needle may be designed so that it is disposed substantially under the distal tip of the anchor.

Figure 8A:
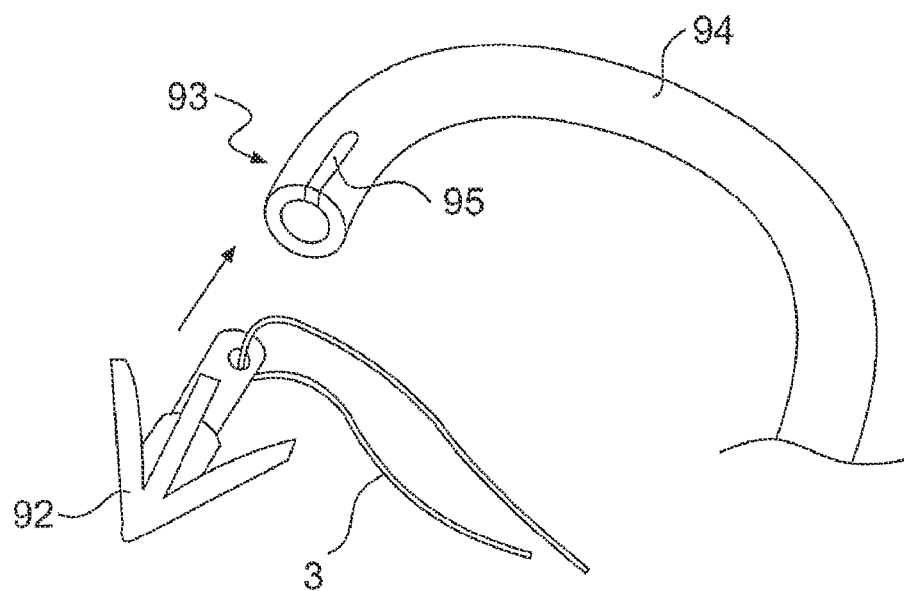
FIGS. 8A-8B illustrate mounting an anchor to an introducer needle, in accordance with various aspects of the present disclosure.
Figure 8B:
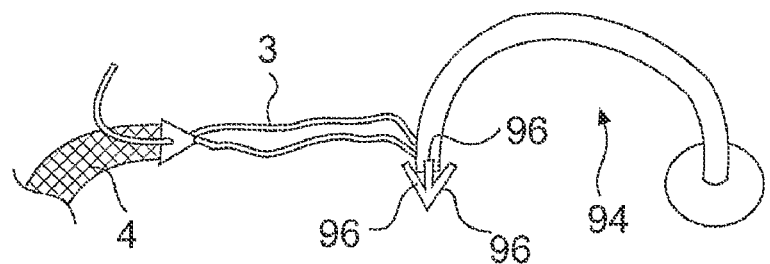
Figure 9:
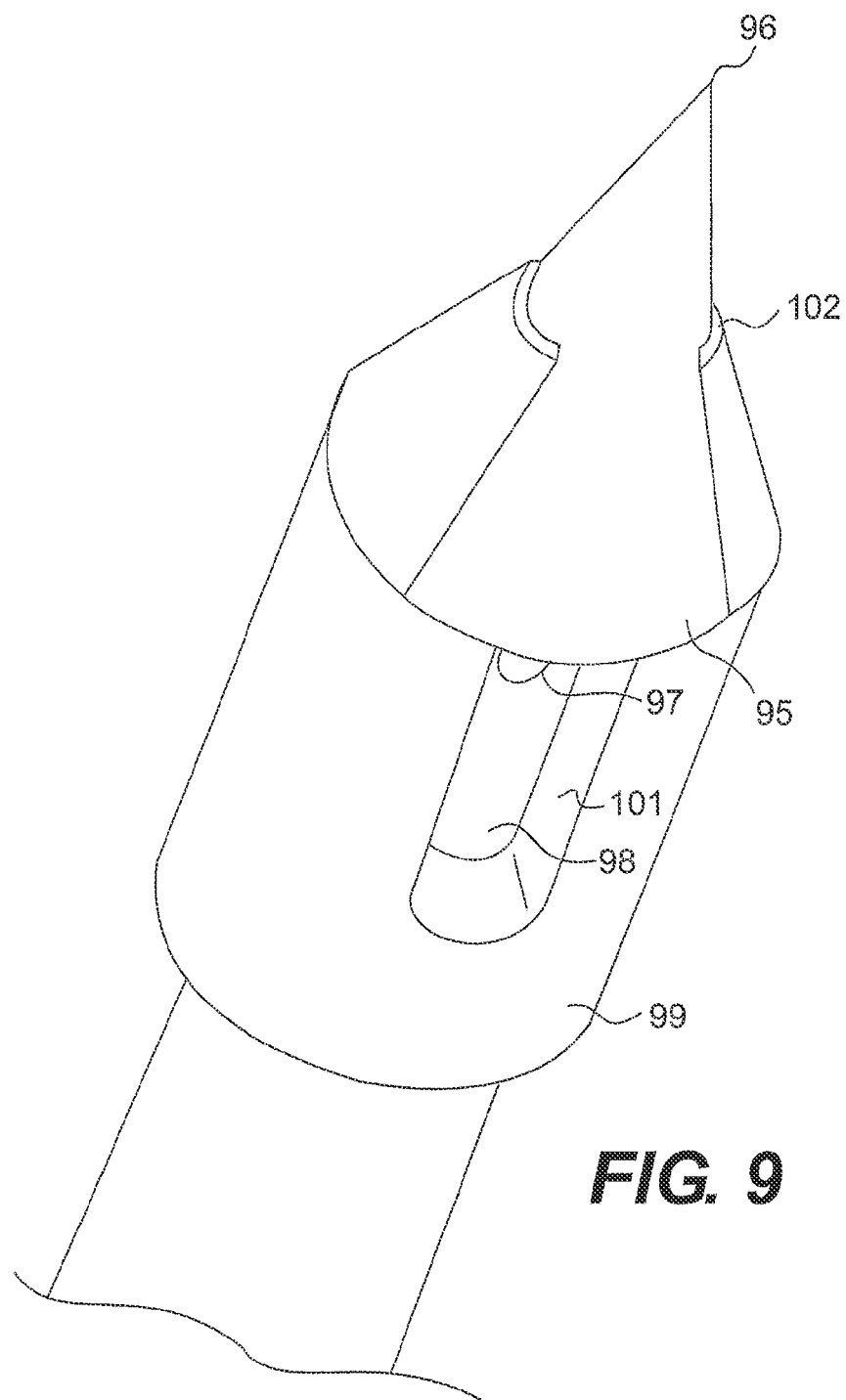
FIG. 9 illustrates another embodiment of an anchor seated in an introducer needle in accordance with various aspects of the present disclosure.

According to another embodiment, and as illustrated in FIGS. 8A and 8B, the anchor barbs may be exposed while the anchor is connected to the distal end of the needle. This configuration is best suited for one-way deployment—that is, the needle may be inserted only in a single direction while connected to the anchor. Anchor 92 can be seated in distal end 93 of introducer needle 94. The distal end comprises a slot 95 for receiving the filamentary element 3. As illustrated in FIG. 11B, which shows an anchor seated in a halo needle, the barbs 96 extend outwardly from the introducer needle 94.

Figure 13:
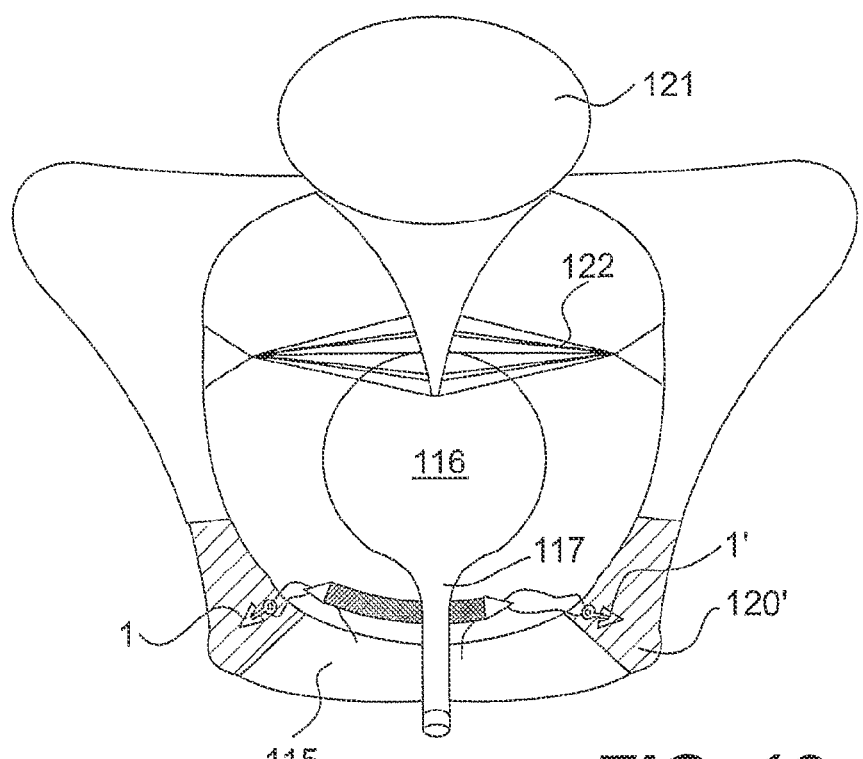
FIG. 13 illustrates an implanted support member, in accordance with various aspects of the present disclosure.

FIG. 13 illustrates a detailed view of an anchor seated in the distal end of a needle. The anchor has a first barb 95, and a second barb (not shown) on the opposite side of the anchor. The anchor has a tip 96 designed to penetrate tissue, an aperture 97 for receiving and holding a filamentary element, and a proximal base portion 98 in which the aperture 97 is disposed. The distal end 99 of the needle comprises at least one slot 101 through which the filamentary element may extend. In order to minimize tissue trauma during insertion of the needle, it can be desirable to have a tight fit between the distal-most end of the needle 102 and the anchor.

Figure 10:
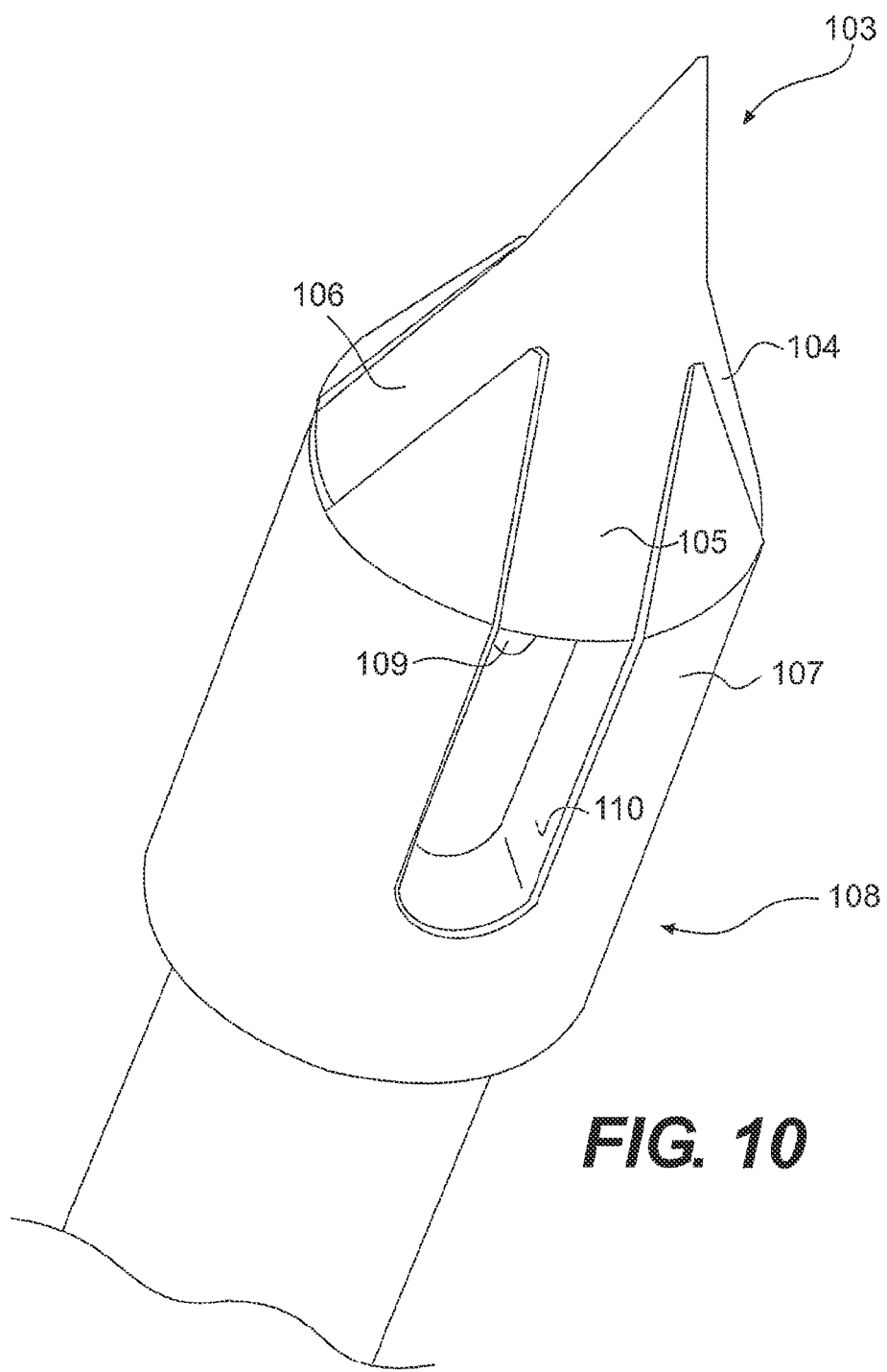
FIG. 10 illustrates another embodiment of an anchor seated introducer needle in accordance with various aspects of the present disclosure.

According to various embodiments, FIG. 10 illustrates a detailed view of an introducer needle having seated therein an anchor 103 with four barbs 104, 105, and 106 (the fourth is not shown). The anchor is designed to fit snugly in the distal end 107 of introducer needle 108. According to various embodiments, anchor 103 contains an aperture 109 through which a filamentary element can be drawn. Distal end of needle 110 contains at least one slot, through which a filamentary element can extend.

Figure 11:
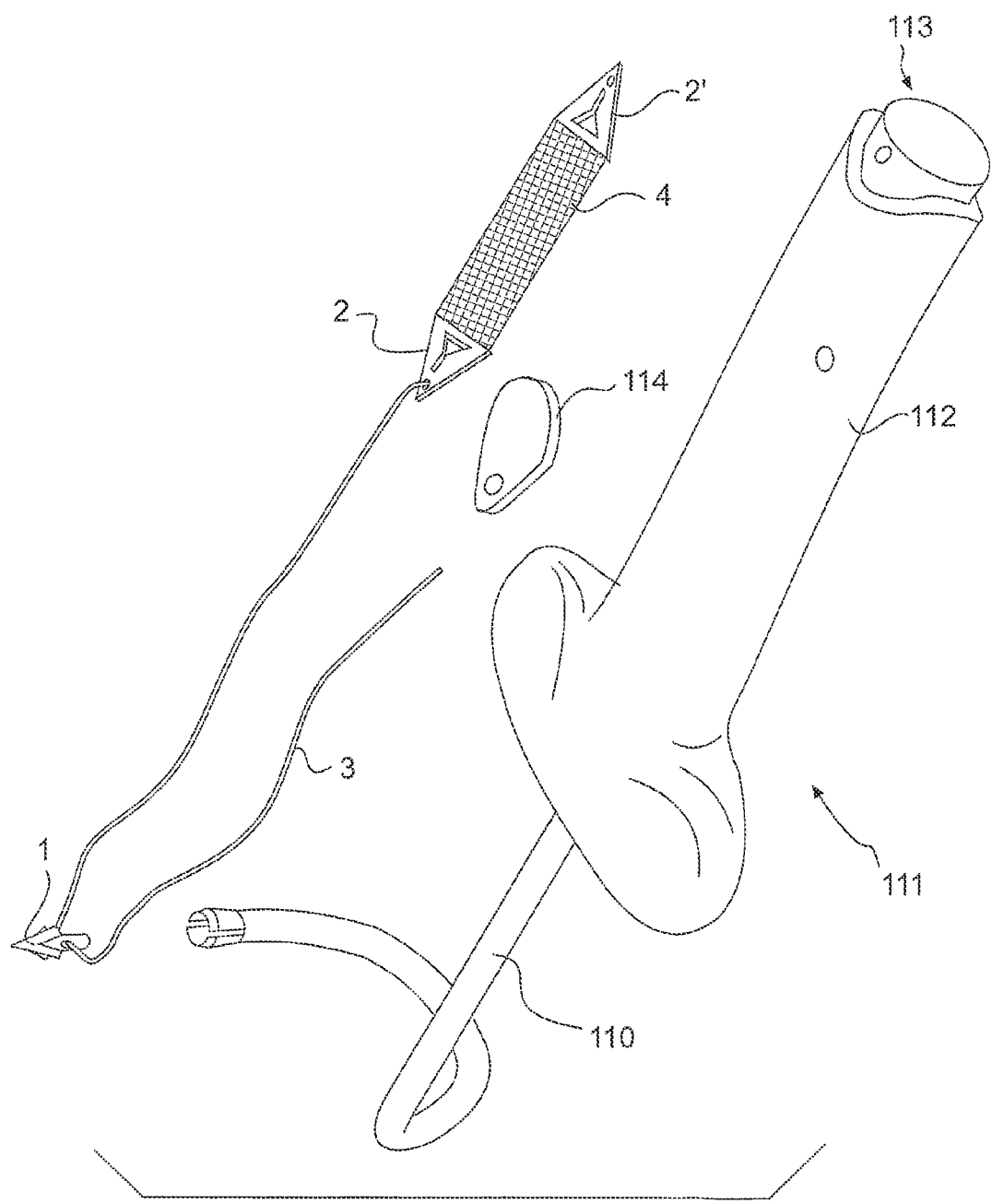
FIG. 11 illustrates one embodiment of certain components of a kit, in accordance with various aspects of the present disclosure.

FIG. 11 illustrates portions of a kit, in accordance with various embodiments, that can be used for implanting a supportive element underneath the urethra. The kit can comprise an introducer needle 111 with a halo-shaped needle shaft 110, a handle 112 and a button 113 for releasing the anchor 1 from the distal end of the needle. Also shown is a filamentary element 3, a support member 4 having two connectors 2 and 2', and a tab 114 that may be secured to the free end of filamentary element 3. According to various embodiments, the kit can further include at least one additional filamentary element and an additional halo needle. According to various embodiments, the needle shaft 110 may be detachable from handle 112, so that a kit may comprise one needle handle 112 and two needle shafts.

According to various embodiments, when the system is used as a sling to support the urethra, an exemplary procedure can comprise at least one of attaching the tissue anchor to an introducer needle, passing the introducer needle through a small vaginal incision beneath the urethra, rotating the introducer needle to insert the anchor into the obturator internus muscle, and releasing the anchor from the introducer needle. The procedure is then repeated on the other side of the urethra so that two anchors are deployed laterally to provide support to the sling. The end of at least one of the filamentary elements is grasped and pulled to position the support member in the desired location, and then secured in the connector via, for example, a cleating element. According to various embodiments, the anchors provide lateral fixation to the sling, while the support member is adjusted independently of the anchor location to provide the desired support. Following the tensioning step, the free ends of the filamentary elements may be trimmed near the connectors to remove excess material. The vaginal incision is then closed, and the procedure is complete.

According to various embodiments, each of the tissue anchors is placed laterally into each obturator internus muscle. The anchors can penetrate into this muscle and fascial lining to provide anchoring outside of, and lateral to, the retropubic space, i.e., the space of Retzius. This region around the obturator membrane has a well-defined anatomical structure, and provides a solid anchoring location for securing tissue anchors. This space is bordered by the inner bony rim of the obturator foramen. According to various aspects of the disclosure, the tissue anchors are not required to pass through the obturator foramina in order to provide sufficient anchoring—only into the obturator internus muscle and/or the obturator membrane.

According to various embodiments, the support members disclosed herein can be inserted via a single vaginal incision. In embodiments where the tissue anchors are secured in the respective obturator internus muscles, the sling arms do not need to exit through skin incisions (which is how the tension exerted by the sling on the urethra is typically adjusted). Instead, the filamentary element is used to adjust the position and tension of the sling.

Figure 12:
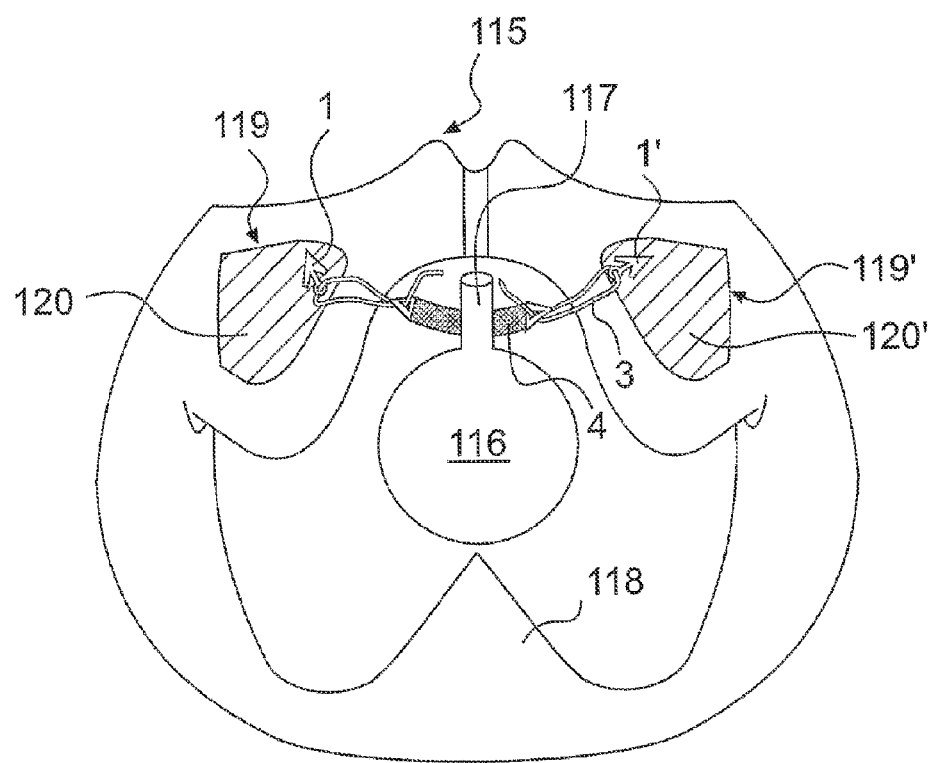
FIG. 12. illustrates a top-down view of a pelvis, with tissue anchors embedded in the obturator internus muscle, in accordance with various aspects of the present disclosure.

FIG. 12 illustrates an exemplary placement of a urethral sling in accordance with various embodiments. With a top-down view of the pelvis from behind, the pubic symphasis 115, bladder 116, urethra 117, sacrum 118, obturator foramina 119 and 119', and obturator internus muscle 120 and 120' can be seen. In accordance with various embodiments, the support member 4 is disposed beneath the urethra 117, and anchors 1 and 1' are secured in the obturator internus muscle.

Figure 14:
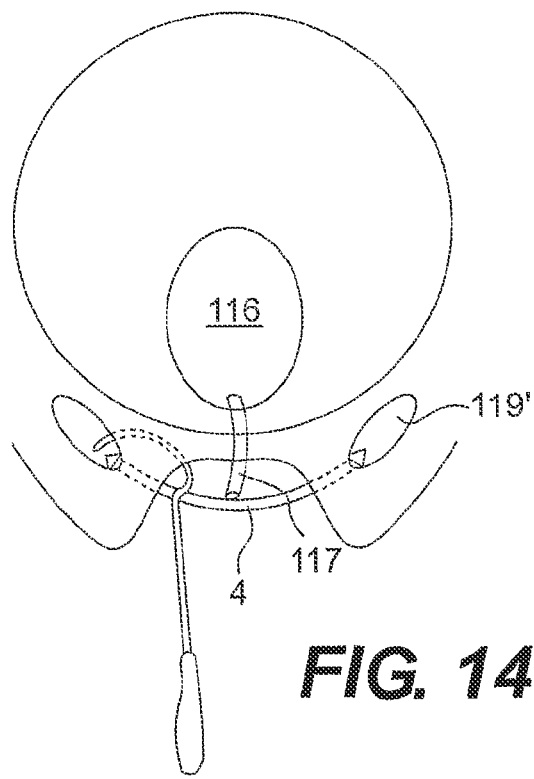
FIG. 14 illustrates an anchor being inserted by an introducer needle, in accordance with various aspects of the present disclosure.

FIG. 13 illustrates a top-down view into the pelvis, including spine 121, and sacrospinous ligament 122. According to various embodiments, anchors 1 and 1' are secured in the obturator internus muscle and optionally into, but not through, the obturator membrane. FIG. 14 illustrates a view showing the placement of anchor 1 into the obturator internus muscle.

Figure 15:
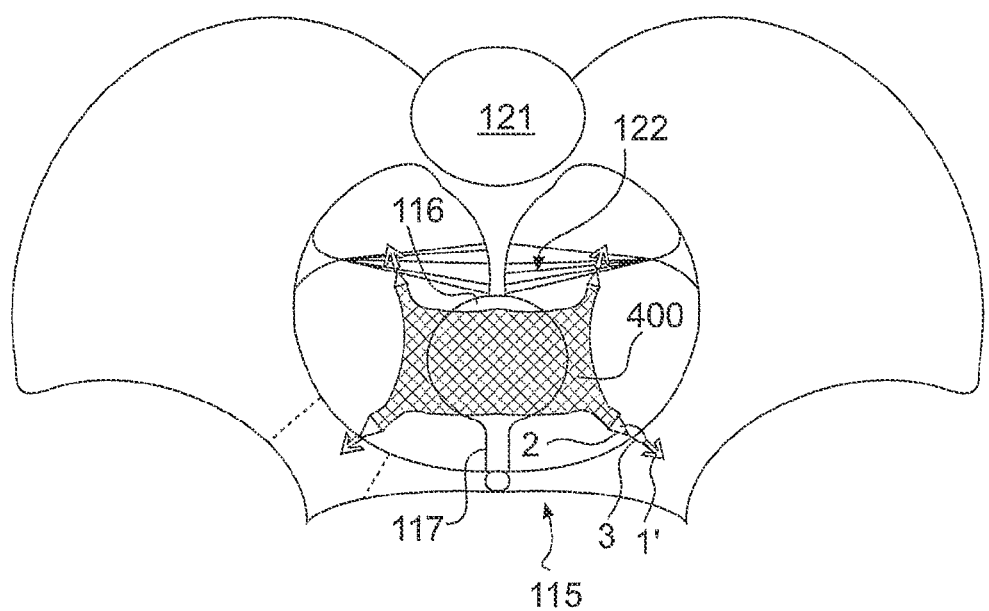
FIG. 15 illustrates a top-down view of a pelvis and an anchored support member supporting the bladder, in accordance with various aspects of the present disclosure.

For applications other than a urethral sling, the support member may have a rectangular or other irregular shape to provide broader support to organs such as the bladder, rectum, bowel, etc. The support member may have multiple arms, with tissue anchors providing multiple points of support around the perimeter of the central support member. The support member may also be positioned at the vaginal apex, with the arms having anchors that are secured to the sacrospinous or uterosacral ligaments to provide apical support to the vaginal vault. According to various embodiments, FIG. 15 illustrates the position of implant 400, which is used for pelvic floor repair.

The particulars shown herein are by way of example and for purposes of illustrative discussion of the various embodiments of the present invention only and are presented in the cause of providing what is believed to be the most useful and readily understood description of the principles and conceptual aspects of the invention. In this regard, no attempt is made to show details of the invention in more detail than is necessary for a fundamental understanding of the invention, the description making apparent to those skilled in the art how several forms of the invention may be embodied in practice.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise. All publications, patent applications, patents, and other references mentioned herein are expressly incorporated by reference in their entirety.

Also, unless otherwise indicated, all numbers expressing quantities of physical parameters and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Numerical ranges given throughout this specification will include every narrower numerical range that falls within such broader numerical range, as if such narrower numerical ranges were all expressly written herein.

What is claimed is:

1. A method for supporting tissue within a patient, comprising:
    making an incision in a vaginal wall of the patient;
    attaching a first tissue anchor to a first introducer needle;
    passing the first introducer needle and the first tissue anchor into the incision in a direction of an obturator membrane, the first tissue anchor attached to a support member via a first filamentary element, the first filamentary element spacing the first tissue anchor from the support member a fixed length;
    inserting the first tissue anchor into the obturator membrane;
    removing the first introducer needle;

attaching a second tissue anchor to a second introducer needle;

passing the second introducer needle and the second tissue anchor into the incision in a direction of a contralateral obturator membrane, the second tissue anchor attached to the support member via a second filamentary element, the second filamentary element having a first end permanently connected to the support member and a second end passing through the second tissue anchor;

inserting the second tissue anchor into the contralateral obturator membrane;

removing the second introducer needle; and pulling on the second filamentary element to adjust tension exerted by the support member on the tissue, wherein the second filamentary element is slidable through an aperture in the second tissue anchor and pulling on the second filamentary element to adjust tension includes sliding at least a portion of the second filamentary element through the aperture.

2. The method according to claim 1, wherein the inserting the first tissue anchor includes passing the first tissue anchor through the obturator membrane.

3. The method according to claim 2, wherein the inserting the second tissue anchor includes passing the second tissue anchor through the contralateral obturator membrane.

4. The method according to claim 1, wherein the tissue is a urethra, and wherein pulling on the second filamentary element to adjust tension includes pulling on the second filamentary element to adjust tension exerted by the support member on the urethra.

5. The method according to claim 1, wherein the tissue is a bladder, and wherein pulling on the second filamentary element to adjust tension includes pulling on the second filamentary element to adjust tension exerted by the support member on the bladder.

6. The method according to claim 1, wherein the tissue is a rectum, and wherein pulling on the second filamentary element to adjust tension includes pulling on the second filamentary element to adjust tension exerted by the support member on the rectum.

7. The method according to claim 1, wherein the first tissue anchor comprises two or more flexible barbs that are in a collapsed position when attached to the first introducer needle and expand to an expanded position with respect to a longitudinal axis of the first tissue anchor when in the obturator membrane.

8. The method according to claim 7, wherein the flexible barbs are parallel to a longitudinal axis of the first tissue anchor in the collapsed position.

9. The method according to claim 1, further comprising:
attaching a third tissue anchor to a third introducer needle;
passing the third introducer needle and the attached third tissue anchor into the incision, the third tissue anchor attached to the support member via a third filamentary element;
inserting the third tissue anchor into tissue of the patient;
removing the third introducer needle.

10. The method according to claim 9, further comprising:
attaching a fourth tissue anchor to a fourth introducer needle;
passing the fourth introducer needle and the attached fourth tissue anchor into the incision, the fourth tissue anchor attached to the support member via a fourth filamentary element;
inserting the fourth tissue anchor into tissue of the patient;
removing the fourth introducer needle.

11. The method according to claim 1, wherein the method is used to treat a rectocele.

12. The method according to claim 1, wherein the method is used to treat a cystocele.

* * * * *